United States Patent
Hattori et al.

(10) Patent No.: US 10,872,411 B2
(45) Date of Patent: Dec. 22, 2020

(54) DIAGNOSTIC IMAGING ASSISTANCE APPARATUS AND SYSTEM, AND DIAGNOSTIC IMAGING ASSISTANCE METHOD

(71) Applicant: HITACHI HIGH-TECHNOLOGIES CORPORATION, Tokyo (JP)

(72) Inventors: Hideharu Hattori, Tokyo (JP); Kenko Uchida, Tokyo (JP); Sadamitsu Aso, Tokyo (JP); Toshinari Sakurai, Tokyo (JP); Yasuki Kakishita, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 84 days.

(21) Appl. No.: 16/340,401

(22) PCT Filed: Oct. 26, 2017

(86) PCT No.: PCT/JP2017/038765
§ 371 (c)(1),
(2) Date: Apr. 9, 2019

(87) PCT Pub. No.: WO2018/084071
PCT Pub. Date: May 11, 2018

(65) Prior Publication Data
US 2019/0236779 A1 Aug. 1, 2019

(30) Foreign Application Priority Data

Nov. 1, 2016 (JP) .................. 2016-214363

(51) Int. Cl.
*G06K 9/00* (2006.01)
*G06T 7/00* (2017.01)
(Continued)

(52) U.S. Cl.
CPC ........... *G06T 7/0012* (2013.01); *G01N 15/00* (2013.01); *G01N 33/48* (2013.01);
(Continued)

(58) Field of Classification Search
CPC ................. G06T 7/0012; G06T 7/0007; G06T 2207/20081; G06T 2207/10056;
(Continued)

(56) References Cited

U.S. PATENT DOCUMENTS 10,748,652 B2 * 8/2020 Yao ..................... A61B 6/5217
10,748,661 B2 * 8/2020 Takata ................... G16H 30/20
(Continued)

FOREIGN PATENT DOCUMENTS

JP       2010-203949 A       9/2010
JP       2010-281637 A      12/2010
(Continued)

*Primary Examiner* — Jose L Couso
(74) *Attorney, Agent, or Firm* — Volpe Koenig

(57) ABSTRACT

A diagnostic imaging assistance apparatus according to the present invention performs a process of inputting images of a tissue and a cell, a process of extracting feature amounts of a wide view and a narrow view from a target image to be processed, a process of classifying whether the target images having different views are normal or abnormal from the feature amounts, and a process of classifying a lesion likelihood using a classification result.

17 Claims, 11 Drawing Sheets

(51) Int. Cl.
*G06T 1/00* (2006.01)
*G16H 30/40* (2018.01)
*G16H 50/20* (2018.01)
*G01N 15/00* (2006.01)
*G01N 33/48* (2006.01)

(52) U.S. Cl.
CPC ........ *G06K 9/00147* (2013.01); *G06T 1/0007* (2013.01); *G16H 30/40* (2018.01); *G16H 50/20* (2018.01); *G06K 9/0014* (2013.01); *G06T 2207/10056* (2013.01); *G06T 2207/20081* (2013.01); *G06T 2207/30024* (2013.01); *G06T 2207/30096* (2013.01)

(58) Field of Classification Search
CPC . G06T 2207/30024; G06T 2207/30096; G06T 2207/10088; G06T 2207/10132; G06T 2207/20016; G06T 2207/20021; G06K 9/00147; G06K 9/0014; G06K 9/4604; G06K 9/00127; G06K 9/6267; G16H 30/40; G16H 50/20; G16H 10/60; G16H 40/67; G01N 15/00; G01N 15/1463; G01N 15/1475; G01N 33/48; G01N 33/4833; G01N 2015/0065; G01N 2015/1006; G02B 21/365; A61B 2560/0431; A61B 2576/00; A61B 5/14546; A61B 5/443; A61B 5/444; A61B 5/6898; A61B 5/0075; C12M 41/36; C12M 41/46; C12M 41/48
See application file for complete search history.

(56) References Cited

U.S. PATENT DOCUMENTS

| | | | |
|---|---|---|---|
| 10,776,963 B2 * | 9/2020 | Schieke | G06T 7/0016 |
| 10,811,134 B2 * | 10/2020 | Bernard | G16H 50/20 |
| 2012/0004514 A1 | 1/2012 | Marugame | |
| 2012/0082366 A1 | 4/2012 | Marugame | |
| 2013/0116511 A1 * | 5/2013 | Sui | G16B 40/00 600/300 |
| 2013/0156279 A1 * | 6/2013 | Schoenmeyer | G06K 9/0014 382/128 |
| 2015/0055844 A1 * | 2/2015 | Molin | G06T 3/4053 382/131 |
| 2015/0310652 A1 * | 10/2015 | Dobson | G06F 3/04845 345/629 |
| 2016/0098589 A1 * | 4/2016 | Brieu | G06K 9/4652 382/128 |
| 2016/0370569 A1 | 12/2016 | Matsumoto | |
| 2017/0270666 A1 * | 9/2017 | Barnes | G06T 7/12 |
| 2018/0053296 A1 | 2/2018 | Hattori et al. | |
| 2018/0089496 A1 * | 3/2018 | Molin | G06K 9/0014 |
| 2018/0322632 A1 * | 11/2018 | Barnes | G06T 7/11 |
| 2020/0258223 A1 * | 8/2020 | Yip | G06T 7/0012 |
| 2020/0272864 A1 * | 8/2020 | Faust | G06K 9/3233 |

FOREIGN PATENT DOCUMENTS

| | | |
|---|---|---|
| JP | 2015-165785 A | 9/2015 |
| JP | 2016-184224 A | 10/2016 |

\* cited by examiner

DIAGNOSTIC IMAGING ASSISTANCE APPARATUS AND SYSTEM, AND DIAGNOSTIC IMAGING ASSISTANCE METHOD

TECHNICAL FIELD

The present invention relates to a diagnostic imaging assistance apparatus, a system, and a diagnostic imaging assistance method and, for example, relates to an image processing technology to detect a specific tissue or a cell (for example, cancer, etc.) included in a captured image of a slice of a tissue/cell on a slide glass by an image capturing device such as a camera in a microscope.

BACKGROUND ART

In recent years, "pathological diagnosis" through a microscope observation of a tissue specimen of a lesion portion occupies an important position in the diagnosis of diseases. In the pathological diagnosis, there needs a lot of labors from creating to diagnosing a specimen, and thus the automation is difficult. In particular, a pathologist's ability and experience is very important in diagnosis. The diagnosis depends on an individual ability. On the other hand, there is a shortage of pathologists at medical sites, including an increase in cancer patients as the population ages. Therefore, needs for an image processing technology and a remote diagnosis for supporting pathological diagnosis is increased. In this way, for example, PTL 1 discloses a technique to determine whether the tissue is pathological for supporting pathological diagnosis. In PTL 1, a low magnification image is generated from a high magnification image, and the image is simply classified by a low magnification image. Then, the pathological tissue is classified using the high magnification image based on the low magnification image.

CITATION LIST

Patent Literature

PTL 1: JP 2010-203949 A

SUMMARY OF INVENTION

Technical Problem

However, in a tissue/cell image, the tissue and the cell have various shapes depending on the type of an abnormal cell (example: cancer) and a progress degree of the abnormal cell (example: cancer). There may be plural suspicious classifications depending on the progress degree of the abnormal cell (example: cancer). Therefore, if the classifications are narrowed to one classification, there may occur a wrong diagnosis. Therefore, as disclosed in PTL 1, even if the low magnification image is generated from the high magnification image, and the image is simply classified by the low magnification image, and then the tissue/cell is classified using the high magnification image based on the low magnification image, there may be an erroneous detection when the classifications are narrowed to one classification. In addition, there is a problem that the tissue/cell is not possible to be classified only by one image of an arbitrary view.

The invention has been made in view of the above problem, and an object thereof is to provide a diagnostic imaging assistance apparatus, a system, and a diagnostic imaging assistance method which can realize the classification of the tissue and the cell from one or more images by calculating a feature amount of the tissue and the cell for the images having different views even in a case where the tissue and the cell have various shapes depending on the type of abnormal tissues and cells (example: cancer) and the progress degree of the abnormal tissues and cells (example: cancer).

Solution to Problem

In the invention to solve the above problem, there is provided a diagnostic imaging assistance apparatus including an input unit configured to receive wide view image data and narrow view image data obtained by capturing a slice of a tissue or a cell of a diagnostic object, a feature extraction unit configured to process the image data input to the input unit to extract a feature amount on an image of the tissue from the wide view image data and extract a feature amount on an image of the cell from the narrow view image data, a single view determination unit configured to classify whether the tissue is normal or abnormal from the feature amount of the wide view image data extracted by the feature extraction unit, and classify whether the cell is normal or abnormal from the feature amount of the narrow view image data, a multiple view determination unit configured to classify a lesion likelihood of the diagnostic object from a classification result of the wide view image data and a classification result of the narrow view image data classified by the single view determination unit, a drawing unit configured to actualize a region containing the tissue or cell classified as abnormal by the multiple view determination unit on the image data, and a recording unit configured to store an image of which the region containing the tissue or cell classified as abnormal is actualized by the drawing unit.

In addition, in the invention to solve the above problem, there is provided a diagnostic imaging assistance method which includes inputting wide view image data obtained by capturing a tissue of a diagnostic object to an input unit, processing the wide view image data input to the input unit by a feature extraction unit to extract a feature amount on an image of the tissue, classifying whether the tissue is normal or abnormal by a single view determination unit from the feature amount of the wide view image data extracted by the feature extraction unit, inputting narrow view image data containing a cell captured from the tissue classified as abnormal by the single view determination unit to the input unit, processing the narrow view image data input to the input unit by a feature extraction unit to extract a feature amount on an image of the cell, classifying whether the cell is normal or abnormal by the single view determination unit from the feature amount of the narrow view image data extracted by the feature extraction unit, classifying a lesion likelihood of the diagnostic object by a multiple view determination unit from a classification result of the wide view image data and a classification result of the narrow view image data classified by the single view determination unit, actualizing a region containing the tissue or the cell classified as abnormal by the single view determination unit on the image data in a drawing unit, and storing the image data obtained by actualizing the region containing the tissue or the cell classified as abnormal in a recording unit.

Further, in the invention to solve the above problem, there is provided a diagnostic imaging assistance method which includes inputting narrow view image data obtained by capturing a cell of a diagnostic object to an input unit, processing the narrow view image data input to the input unit by a feature extraction unit to extract a feature amount on an image of the cell, classifying whether the cell is normal or abnormal by a single view determination unit from the feature amount of the narrow view image data extracted by the feature extraction unit, capturing an image of a tissue containing a cell classified as abnormal by the single view determination unit to input wide view image data of the tissue to the input unit, processing the wide view image data input to the input unit by a feature extraction unit to extract a feature amount on an image of the tissue, classifying whether the tissue is normal or abnormal by the single view determination unit from the feature amount of the wide view image data extracted by the feature extraction unit, classifying a lesion likelihood of the diagnostic object by a multiple view determination unit from a classification result of the narrow view image data and a classification result of the wide view image data classified by the single view determination unit, actualizing a region containing the cell or the tissue classified as abnormal by the single view determination unit on the image data in a drawing unit, and storing the image data obtained by actualizing the region containing the cell or the tissue classified as abnormal in a recording unit.

Further, in the invention to solve the above problem, there is provided a remote diagnostic assistance system which includes an image acquisition device equipped with an image capturing device to capture image data, and a server which includes the diagnostic imaging assistance apparatus. The image acquisition device transmits the image data to the server. The server stores the images of the tissue and the cell determined by processing the received image data by the diagnostic imaging assistance apparatus and the determination result in a memory, and transmits the images and the determination result to the image acquisition device. The image acquisition device displays the received images of the tissue and the cell determined and the determination result on the display device.

In addition, in the invention to solve the above problem, a network entrusting service provision system includes an image acquisition device equipped with an image capturing device to capture image data, and a server which includes the diagnostic imaging assistance apparatus. The image acquisition device transmits the image data to the server. The server stores the images of the tissue and the cell determined by processing the received image data using the diagnostic imaging assistance apparatus and an identifier in a memory, and transmits the identifier to the image acquisition device. The image acquisition device stores the received identifier. The diagnostic imaging assistance apparatus in the image acquisition device determines the image of the other tissues and cells using the identifier, and displays the determination result on the display device.

Advantageous Effects of Invention

According to the invention, even in a case where the shapes of tissues and cells are variously changed depending on the type of an abnormal tissue and an abnormal cell (example: cancer) and the progress degree of the abnormal tissue and the abnormal cell (example: cancer), a feature amount of the tissue and the cell is calculated for regions having different views. Therefore, an erroneous detection and an excessive detection can be suppressed, and the tissue/cell can be classified from one or more images.

Other features of the invention will be clear from the description and the accompanying drawings. In addition, embodiments of the invention are achieved and realized by elements, combinations of various elements, the following detailed description, and the attached claims.

It is necessary to understand that the description of this specification is given only as a typical example, and does not limit the scope of claims or applications of the invention.

DESCRIPTION OF EMBODIMENTS

Embodiments of the invention provide a diagnostic imaging assistance apparatus and a method thereof in which a deformed degree of a tissue or a cell, determines the presence/absence of an abnormal tissue (example: lesion) for each different-view region to calculate likelihood of the abnormal tissue (example: lesion), and determines the presence/absence of an abnormal cell and the likelihood of the abnormal cell (example: lesion) from the determination result of the different-view region, so that detection omission and erroneous detection of the abnormal tissue and the abnormal cell (example: lesion) are suppressed.

The diagnostic imaging assistance apparatus according to the invention performs a process of extracting feature amounts of different views of a target image, a process of determining whether the image of each view corresponds to one classification using the plurality of feature amounts, and a process of determining whether the determination process is ended with respect to the plurality of views.

Hereinafter, embodiments of the invention will be described with reference to the accompanying drawings. In the accompanying drawings, the elements having the same function may be attached with the same symbol. Further, the accompanying drawings illustrate specific embodiments and mounting examples according to the principle of the invention in order to help with understanding of the invention, but the invention is not interpreted in a limited way.

In this embodiment, the explanation has been made in detail sufficiently for a person skilled in the art to implement the invention while other mounting/embodiments may be possible. It is necessary to understand that changes in configuration/structures and replacements of various elements may be implemented without departing from a scope of the technical ideas and the spirit of the invention. Therefore, the following description must not be interpreted in a limited way.

Further, embodiments of the invention may be mounted in software which is executed on a general purpose computer, in dedicated hardware, or in a software and hardware combination as described below.

In the following, the description will be given about processes in embodiments of the invention using "processing units (for example, a feature extraction unit, etc.) as programs" as a subject (operation subject). However, the program performs the process to be performed by a processor (CPU, etc.) while using a memory and a communication port (communication control device). Therefore, the description may be given using the processor as a subject.

First Embodiment

<Functional Configuration of Diagnostic Imaging Assistance Apparatus>

Figure 1:
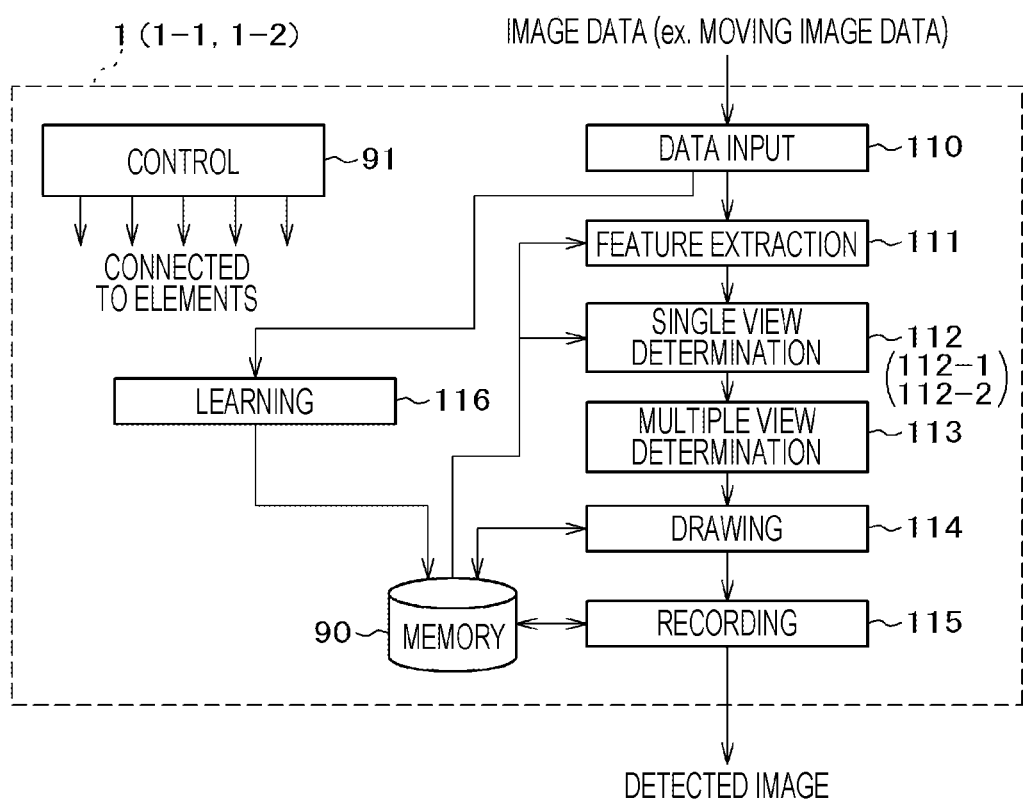
FIG. 1 is a block diagram illustrating a function of a diagnostic imaging assistance apparatus according to first to third embodiments of the invention.

FIG. 1 is a block diagram illustrating a functional configuration of a diagnostic imaging assistance apparatus 1 according to this embodiment. The diagnostic imaging assistance apparatus 1 according to this embodiment has the functions of a data input 110, a feature extraction 111, a single view determination 112, a multiple view determination 113, a drawing 114, a recording 115, a learning 116, a control 91, and a memory 90. The diagnostic imaging assistance apparatus 1 may be mounted in a tissue/cell image acquisition device such as a virtual slide, or may be mounted in a server connected to the tissue/cell image acquisition device through a network as described below (fourth and fifth embodiments).

In the diagnostic imaging assistance apparatus 1, the functions of the data input 110, the feature extraction 111, the single view determination 112, the multiple view determination 113, the drawing 114, the recording 115, and the learning 116 may be realized by a program, or may be realized as modules.

As the data input 110, image data is input. For example, the data input 110 may acquire encoded still image data of a JPG, Jpeg 2000, PNG, or BMP format captured at an interval of a predetermined time by an image pickup unit such as a camera built in a microscope, and the image may be used as an input image. In addition, still image data of a predetermined interval of frame may be extracted as the data input 110 from moving image data of a Motion JPEG, MPEG, H.264, or HD/SDI format, and the image may be used as an input image. In addition, the data input 110 may use an image acquired through a bus or a network by the image pickup unit as an input image. In addition, the data input 110 may use an image stored in a detachable recording medium as an input image.

The feature extraction 111 is a function of extracting a feature amount related to a tissue or a cell from the image.

The single view determination 112 is a function of calculating a deformed degree of a tissue or a cell from the extracted feature amount, and classifying whether the tissue is a normal tissue or an abnormal tissue, or whether the cell is a normal cell or an abnormal cell in the single view.

The multiple view determination 113 is a function of classifying a tissue/cell using a plurality of single-view classification results.

The drawing 114 is a function of drawing a detection frame on the image to surround the abnormal tissue or the abnormal cell which is classified by the multiple view determination 113.

The recording 115 is a function of storing the image of the detection frame drawn on the original image by the drawing 114 in the memory 90.

The learning 116 is a function of calculating each parameter (a filter factor, an offset value, etc.) required for the identification in a machine learning to identify a normal tissue or cell as a normal tissue or cell, or an abnormal tissue or cell and an abnormal tissue or cell.

The control 91 is realized by a processor which is connected to each element in the diagnostic imaging assistance apparatus 1. The operation of each element of the diagnostic imaging assistance apparatus 1 is performed autonomously by the above-described components or performed by a command of the control 91.

In this way, in the diagnostic imaging assistance apparatus 1 of this embodiment, the normal cell or the abnormal cell (or the normal tissue or the abnormal tissue) is classified with respect to the single view by the single view determination 112 using the feature amount indicating the deformed degree of the tissue or the cell obtained by the feature extraction 111. The tissue and the cell are classified using the plurality of single-view classification results by the multiple view determination 113.

<Hardware Configuration of Diagnostic Imaging Assistance Apparatus>

Figure 2:
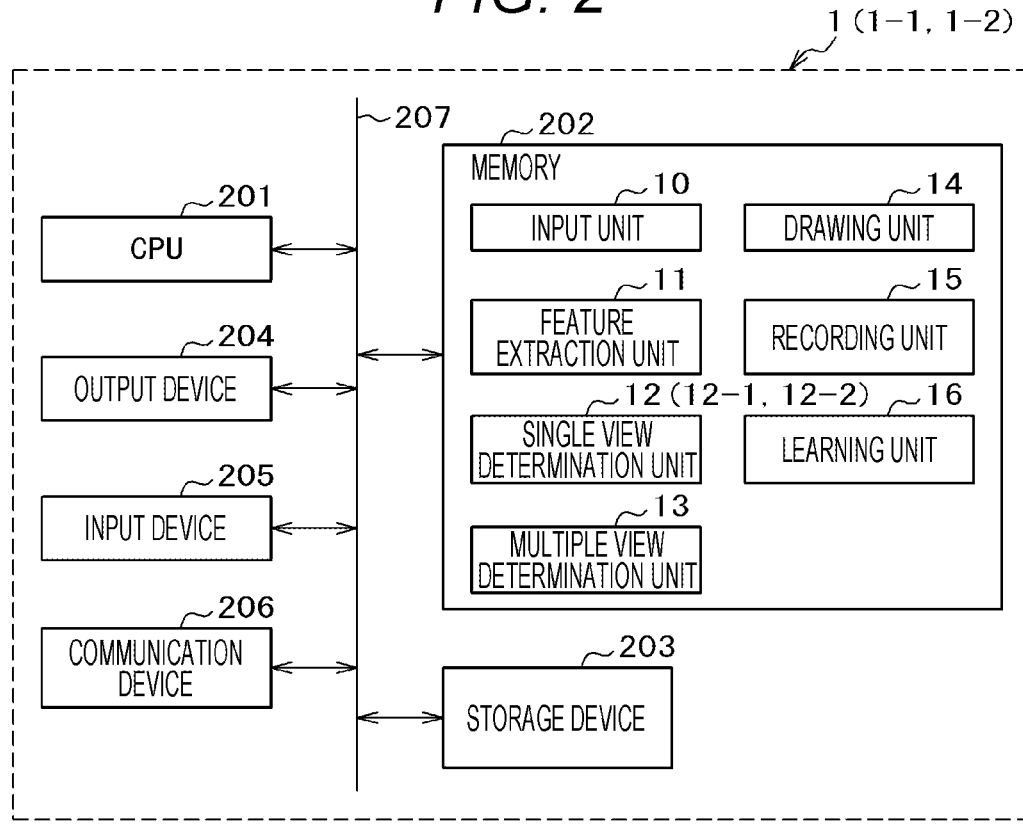
FIG. 2 is a block diagram illustrating an exemplary hardware configuration of the diagnostic imaging assistance apparatus according to the first to third embodiments of the invention.

FIG. 2 is a diagram illustrating an exemplary hardware configuration of the diagnostic imaging assistance apparatus 1 according to the embodiment of the invention.

The diagnostic imaging assistance apparatus 1 includes a CPU (processor) 201 to perform various types of programs, a memory 202 to store various types of programs, a storage device (corresponding to the memory 90) 203 to store various types of data, an output device 204 to output a detected image, an input device 205 to input a user's command and an image, and a communication device 206 to communicate with other devices, and these are connected to each other through a bus 207.

The CPU 201 reads and performs various types of programs from the memory 202 as needed.

The memory 202 stores, as programs, an input unit 10, a feature extraction unit 11, a single view determination unit 12, a multiple view determination unit 13, a drawing unit 14, a recording unit 15, and a learning unit 16.

The input unit 10 has a function of the data input 110 in the functional configuration illustrated in FIG. 1. The feature extraction unit 11 has a function of the feature extraction 111. The single view determination unit 12 has a function of the single view determination 112. The multiple view determination unit 13 has a function of the multiple view determination 113. The drawing unit 14 has a function of the drawing 114. The recording unit 15 has a function of the recording 115. The learning unit 16 has a function of the learning 116.

The storage device 203 stores a processing target image, the single-view classification result and a numerical value generated by the single view determination unit 12, the classification result of the tissue/cell generated by the multiple view determination unit 13, position information to draw the detection frame generated by the drawing unit 14, and various types of parameters of the following Expressions (Math. 1 and Math. 2) generated by the learning unit 16.

The output device 204 is configured by devices such as a display, a printer, and a speaker. For example, the output device 204 displays data generated by the drawing unit 14 on a display screen.

The input device 205 is configured by devices such as a keyboard, a mouse, and a microphone. A user's command (including a determination of the processing target image) is input to the diagnostic imaging assistance apparatus 1 by the input device 205.

In a case where the communication device is included in a personal computer connected to a tissue/cell image acquisition device as the communication device 206, the diagnostic imaging assistance apparatus 1 may not include the communication device 206 which is not an essential configuration of the diagnostic imaging assistance apparatus 1. For example, the communication device 206 receives data (including an image) transmitted from other device (for example, a server) connected through a network, and performs an operation of storing the data in the storage device 203.

Figure 3A:
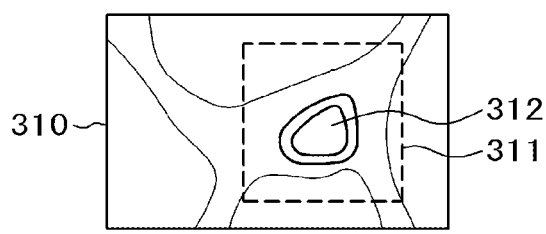
FIG. 3A is a diagram illustrating a wide view image in the first embodiment of the invention.
Figure 3B:
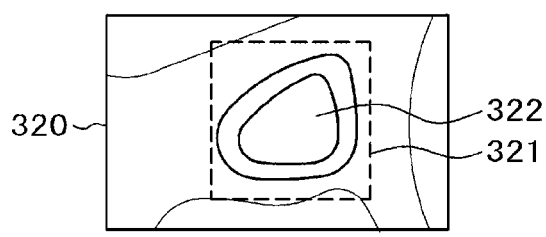
FIG. 3B is a diagram illustrating a narrow view image in the first embodiment of the invention.

The diagnostic imaging assistance apparatus 1 according to this embodiment detects the normality/abnormality and an abnormal place of a tissue containing a cell from a wide view image 310 (histopathological image) as illustrated in FIG. 3A. Next, a narrow view image 320 illustrated in FIG. 3B is obtained with respect to the detected abnormal place. Then, the normality/abnormality and the abnormal place of the cell is detected from the narrow view image 320, and a lesion likelihood is determined from the normality/abnormality and the abnormal place thus detected.

Figure 20:
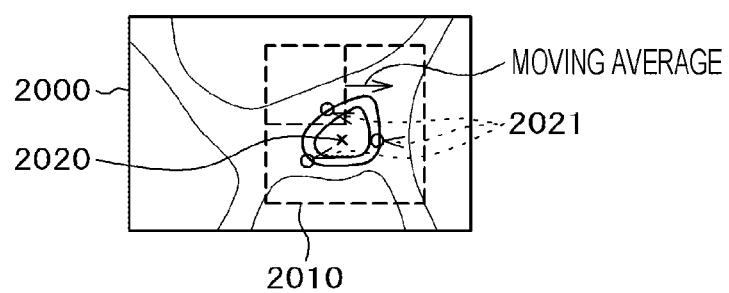
FIG. 20 is a diagram illustrating an image for describing the center of a distribution of a lesion likelihood in the wide view image of a single view determination unit 12 in the first embodiment of the invention.

In the diagnostic imaging assistance apparatus 1 according to this embodiment, the single view determination unit 12 determines a representative pixel from the abnormal place detected in the wide view image illustrated in FIG. 3A and creates a high resolution image corresponding to the representative pixel, or retrieves a high magnification image corresponding to the representative pixel to acquire the narrow view image illustrated in FIG. 3B. The representative pixel is an arbitrary pixel in the abnormal place in the wide view image, a pixel having a maximum lesion likelihood, or a pixel at the center of the distribution of the lesion likelihood. For example, the distribution center is a pixel 2020 in which the calculation result of a moving average of the distribution of a lesion-causing place 2021 in the region surrounded by a detection frame 2010 of a wide view image 2000 is maximum as illustrated in FIG. 20.

<Configuration and Operation of Units>

Hereinafter, the configuration and the operation of each element will be described.

(i) Feature Extraction Unit 11

The feature extraction unit 11 obtains feature amounts of a plurality of views. As an example, FIGS. 3A and 3B illustrate an example in which the feature amount of the narrow view image is obtained from the wide view image. For example, the feature amount of a tissue 312 is obtained from a view 1 surrounded by a detection frame 311 of the wide view (low resolution of low magnification) image 310 of FIG. 3A. As an example, a filter 400 obtaining the feature amount of an any tissue shape is illustrated in FIG. 4.

Figure 4:
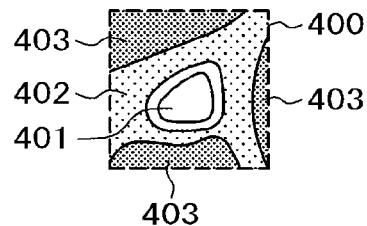
FIG. 4 is a diagram illustrating an image for describing an exemplary filter of the wide view image in the first embodiment of the invention.

For example, filter factors wj of region 1:401, region 2:402, and region 3:403 of the filter 400 illustrated in FIG. 4 are set to 0, 1, and −1 respectively. In addition, the filter factor obtained by the machine learning may be set to wj to identify a normal tissue as a normal tissue, or to identify an abnormal tissue as an abnormal tissue.

In other words, the filter factor wj is a coefficient as illustrated in Expression (Math. 1). In Expression (Math. 1), pj represents a pixel value, wj represents a filter factor, bi represents an offset value, m represents the number of filter factors, and h represents a non-linear function.

Figure 5:
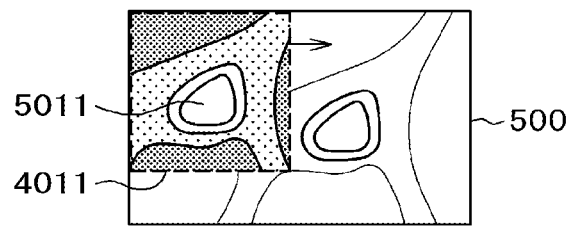
FIG. 5 is a diagram illustrating an image for describing a state where the filter is moved in one direction on the wide view image in the first embodiment of the invention.
Figure 6:
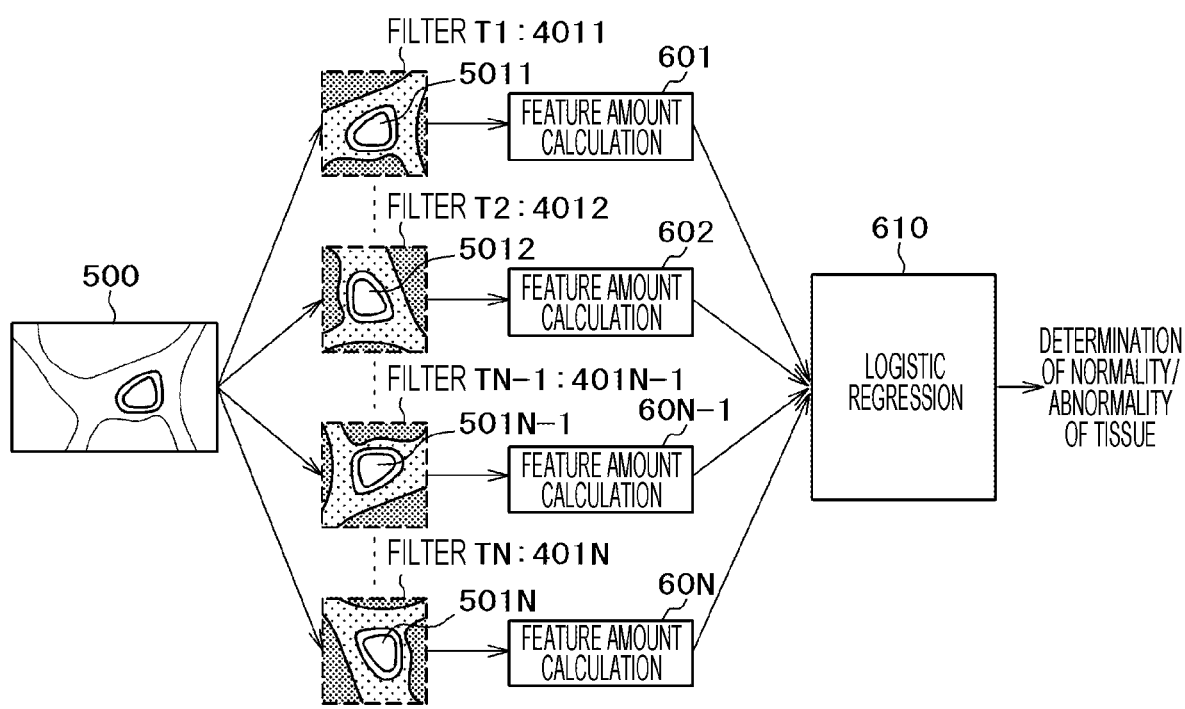
FIG. 6 is a flowchart illustrating a processing flow in which a plurality of filters is operated on the wide view image in the first embodiment of the invention to determine normality/abnormality of a tissue.

As illustrated in FIG. 5, using Expression (Math. 1), the calculation result of a filter 4011 at each position is obtained for a place from the left upper portion to the right lower portion of a target image 500 (wide view image), so that a feature amount fi of a filter i (i=T1) having the shape of an arbitrary tissue 5011 is obtained. Similarly, as illustrated in FIG. 6, the feature amounts fi (i=2 to N) of filters T2:4012 to TN:401N are calculated using the calculation result obtained in each place of the left upper and right lower portions of the target image 500 (wide view image) with respect to the filters which obtain the feature amount of the shapes of arbitrary tissues 5012 to 501N of filters T2:4012 to TN:401N.

A range size of the view 1 of the target image 500 (wide view image) is set to a range size at which the machine learning is performed plural times while changing the range size of the view 1 and an identification accuracy to an evaluation data set is maximized in a case where the machine learning is used for example.

[Math. 1]

$$fi = h\left(\sum_{j=1}^{m} (pj \times wj) + bi\right)$$ (Math. 1)

Figure 7:
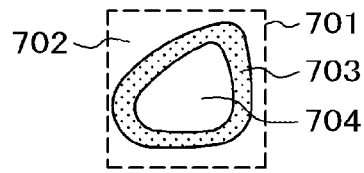
FIG. 7 is a diagram illustrating an image for describing an exemplary filter of the narrow view image in the first embodiment of the invention.

In addition, for example, the feature amount of a cell 322 is obtained from a view 2 surrounded by a detection frame 321 of the narrow view (high resolution or high magnification) image 320 of FIG. 3B. As an example, a filter obtaining the feature amount of an any cell shape is illustrated in FIG. 7. For example, in a filter 701 illustrated in FIG. 7, the filter factors wj of region 4:702 corresponding to the outside of the cell, region 5:703 corresponding to a cell boundary, region 6:704 corresponding to the inner portion of the cell are set to 0, 1, and −1 respectively. In addition, the filter factor obtained by the machine learning may be set to wj to identify a normal cell as a normal cell, or to identify an abnormal cell as an abnormal cell. In other words, the filter factor wj is a coefficient as illustrated in Expression (Math. 1).

Figure 8:
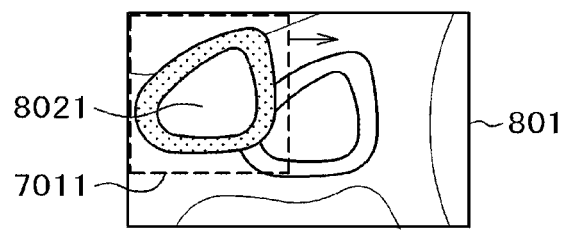
FIG. 8 is a diagram illustrating an image for describing a state where the filter is moved in one direction on the narrow view image in the first embodiment of the invention.
Figure 9:
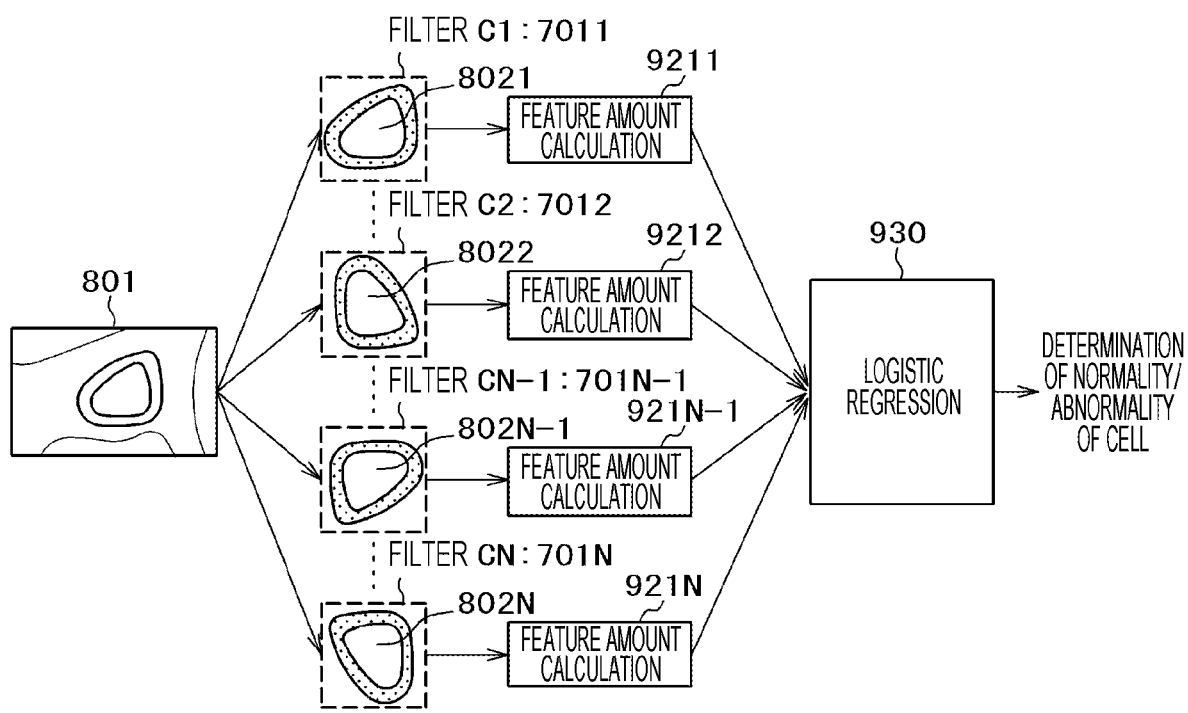
FIG. 9 is a flowchart illustrating a processing flow in which a plurality of filters is operated on the narrow view image in the first embodiment of the invention to determine normality/abnormality of a cell.

As illustrated in FIG. 8, using Expression (Math. 1), the calculation result of the filter 7011 at each position is obtained for a place from the left upper portion to the right lower portion of a target image 801 (histopathological image), and the feature amount fi of the filter i having the shape (i=C1) of an arbitrary cell (feature amount calculation 9211). Similarly, as illustrated in FIG. 9, the feature amounts of the filters 7012 to 701N are calculated using the filters 7012 to 701N which obtains the feature amounts of the shapes of the arbitrary cells 8022 to 802N from C2 to CN (9212 to 921N).

A range size of the view 2 of the target image 801 (narrow view image) is set to a range size at which the machine learning is performed plural times while changing the range size of the view 2 and an identification accuracy to an evaluation data set is maximized in a case where the machine learning is used for example.

(ii) Single View Determination Unit 12

The single view determination unit 12 classifies whether the tissue in the input tissue/cell image is normal or abnormal by Expression (Math. 2) using each feature amount fi from the plurality of filters T1 to TN which relate to the shape of arbitrary tissue obtained by the feature extraction unit 11 as illustrated in FIG. 6. In Expression (Math. 2), w represents an array of weights, f represents an array of feature amounts fi obtained by each filter from the input image, b represents the offset value, g represents a non-linear function, and y represents a calculation result. The weight w and the offset value b are obtained by the learning unit 16 through the machine learning.

Similarly, the single view determination unit 12 classifies whether the cell in the input tissue/cell image is normal or abnormal by Expression (Math. 2) using each feature amount fi from the plurality of filters C1 to CN which relate to the shape of arbitrary cell obtained by the feature extraction unit 11 as illustrated in FIG. 9.

[Math. 2]

$$|y = g(w \times f + b)|$$ (Math. 2)

(iii) Learning Unit 16

For example, the learning unit 16 learns the deformed degree of the tissue or the cell using the technique of the machine learning of the related art. For example, if it is determined that the tissue in the input tissue/cell image is a normal tissue by Expression (Math. 2), the tissue is classified into a normal tissue by a logistic regressive process in a logistic regressive processing unit 610. If it is determined that the cell in the input tissue/cell image is a normal cell, the cell is classified into a normal cell by the logistic regressive process in a logistic regressive processing unit 930.

In addition, the deformed degree of the tissue or the cell is learned. For example, if the tissue in the input tissue/cell image is an abnormal tissue, the tissue is classified into an abnormal tissue by the logistic regressive process. If the cell in the input tissue/cell image is an abnormal cell, the cell is classified into an abnormal cell by the logistic regressive process. For example, as a technique of the machine learning, a convolutional neural network may be used.

The learning unit 16 repeatedly operates the feature extraction unit 11 and the single view determination unit 12 using the plurality of learning images, obtains the weight w, the filter factor wj, and the offset values b and bi of Expressions (Math. 1 and Math. 2), and creates an identifier to classify whether the tissue is a normal tissue or an abnormal tissue and an identifier to classify whether the cell is a normal cell or an abnormal cell. In addition, the learning unit 16 stores the weight w, the filter factor wj, and the offset values b and bi in the memory.

(iv) Multiple View Determination Unit 13

The multiple view determination unit 13 displays a classification result of a lesion likelihood using a lesion value of the abnormal tissue (example: lesion) obtained from the wide view image by the single view determination unit 12 and a likelihood value of the abnormal cell (example: lesion) obtained from the narrow view image. As an example, a benign lesion likelihood and a malignant lesion likelihood of the cell are classified in the narrow view image.

Further, not only the narrow view image but also the type of the malignancy may be not able to be classified. Therefore, the lesion likelihood of the tissue is classified in the wide view image, and the type of the malignance can be classified in combination with the classification result of the narrow view image.

For example, the presence/absence (normality, benignancy, or malignancy) of the lesion of a breast cell is classified in the narrow view image. In the case of the malignancy, it is classified into the types (a cribriform type, a comedo type, a solid type, a papillary type, etc.) of malignancy in the wide view image. In addition, for example, the presence/absence (normality, cancer, etc.) of the lesion of a stomach cell is classified in the narrow view image. An invasion depth is classified in the wide view image. A progress degree (an early stomach cancer (a cancer is spread up to a lower layer of the mucous membrane), a progressive stomach cancer (a cancer is spread over the muscle coat exceeding the mucous membrane), etc.) of cancer is classified. In addition, for example, the presence/absence (normality, cancer, etc.) of the lesion of the breast cell is classified in the narrow view image, and the presence/absence of invasion (non-invasion, invasion, etc.) is classified in the wide view image.

(v) Drawing Unit 14

Figure 10:
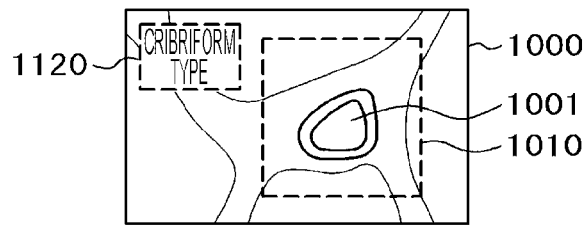
FIG. 10 is a diagram illustrating an image of a state where a place suspected of an abnormal tissue is surrounded by a detection frame on the wide view image in the first embodiment of the invention.

In a case where the tissue is classified into the abnormal tissue in the wide view image in the single view determination unit 12, the drawing unit 14 draws a detection frame 1010 to surround the place 1001 suspected of the abnormal tissue in a target image 1000 (the input wide view image) in order to show a place 1001 suspected of the abnormal tissue as illustrated in FIG. 10. On the other hand, in a case where the tissue is classified into the normal tissue, the detection frame is not drawn on the input target image, but the target image 1000 (the wide view image) is displayed as it is.

Figure 11:
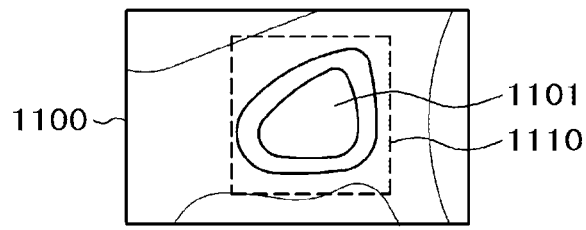
FIG. 11 is a diagram illustrating an image of a state where a place suspected of an abnormal cell is surrounded by a detection frame on the narrow view image in the first embodiment of the invention.

In addition, in a case where the cell is classified into the abnormal cell in a target image 1100 (the narrow view image), a detection frame 1110 surrounding the place 1101 suspected of the abnormal cell is drawn in the target image 1100 (the input narrow view image) in order to show a place 1101 suspected of the abnormal cell as illustrated in FIG. 11. On the other hand, in a case where the cell is classified into the normal cell, the detection frame is not drawn on the input target image, but the input target image 1100 is displayed as it is. In addition, as illustrated in FIG. 10, a result (for example, the cribriform type) of the lesion likelihood classified in the wide view image and the narrow view image is displayed in a determination result display region 1120.

(vi) Recording Unit 15

The recording unit 15 stores coordinate information for drawing the detection frames (311, 321, 1010, and 1110) on the input target image by the drawing unit 14 and the target image in the memory 90.

<Processing Procedure of Diagnostic Imaging Assistance Apparatus>

Figure 12:
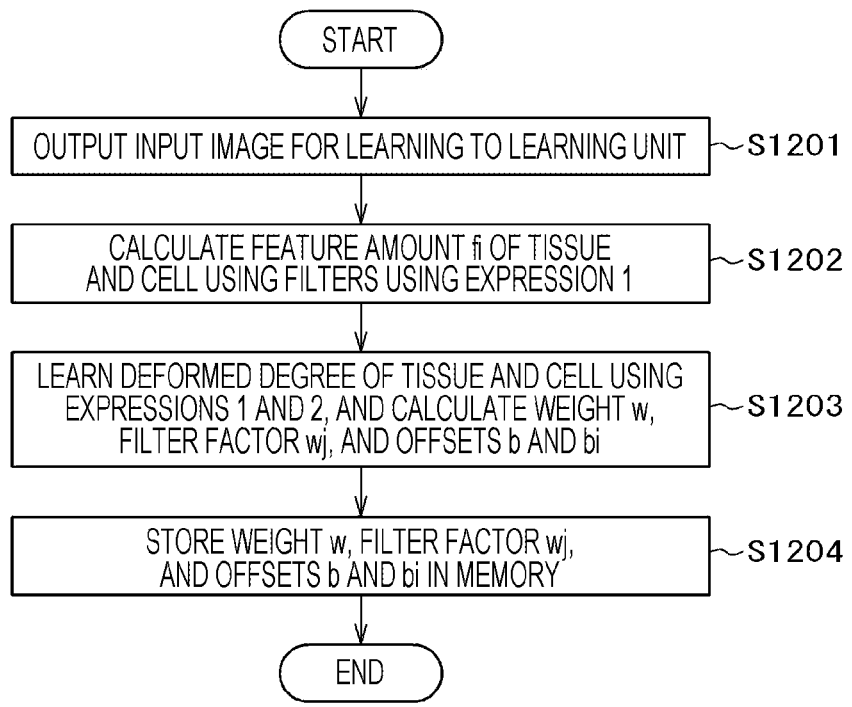
FIG. 12 is a flowchart for describing an operation of a learning unit 16 in the first embodiment of the invention.

FIG. 12 is a flowchart for describing an operation of the learning unit 16 of the diagnostic imaging assistance apparatus according to the embodiment of the invention. In the following, the description will be given about the learning unit 16 as the operation subject, but the CPU 201 may be replaced as the operation subject and the processing units as programs.

(i) Step: S1201

The input unit 10 receives an image input for learning, and outputs the input image to the learning unit 16.

(ii) Step: S1202

The learning unit 16 obtains the feature amount fi of the tissue or the cell using a plurality of filters using the above Expression 1.

(iii) Step: S1203

The learning unit 16 learns the deformed degree of the tissue or the cell using Expressions 1 and 2, and calculates the weight w, the filter factor wj, and the offsets b and bi.

(iv) Step: S1204

The learning unit 16 stores the weight w, the filter factor wj, and the offsets b and bi which are calculated in the memory 90.

Figure 13:
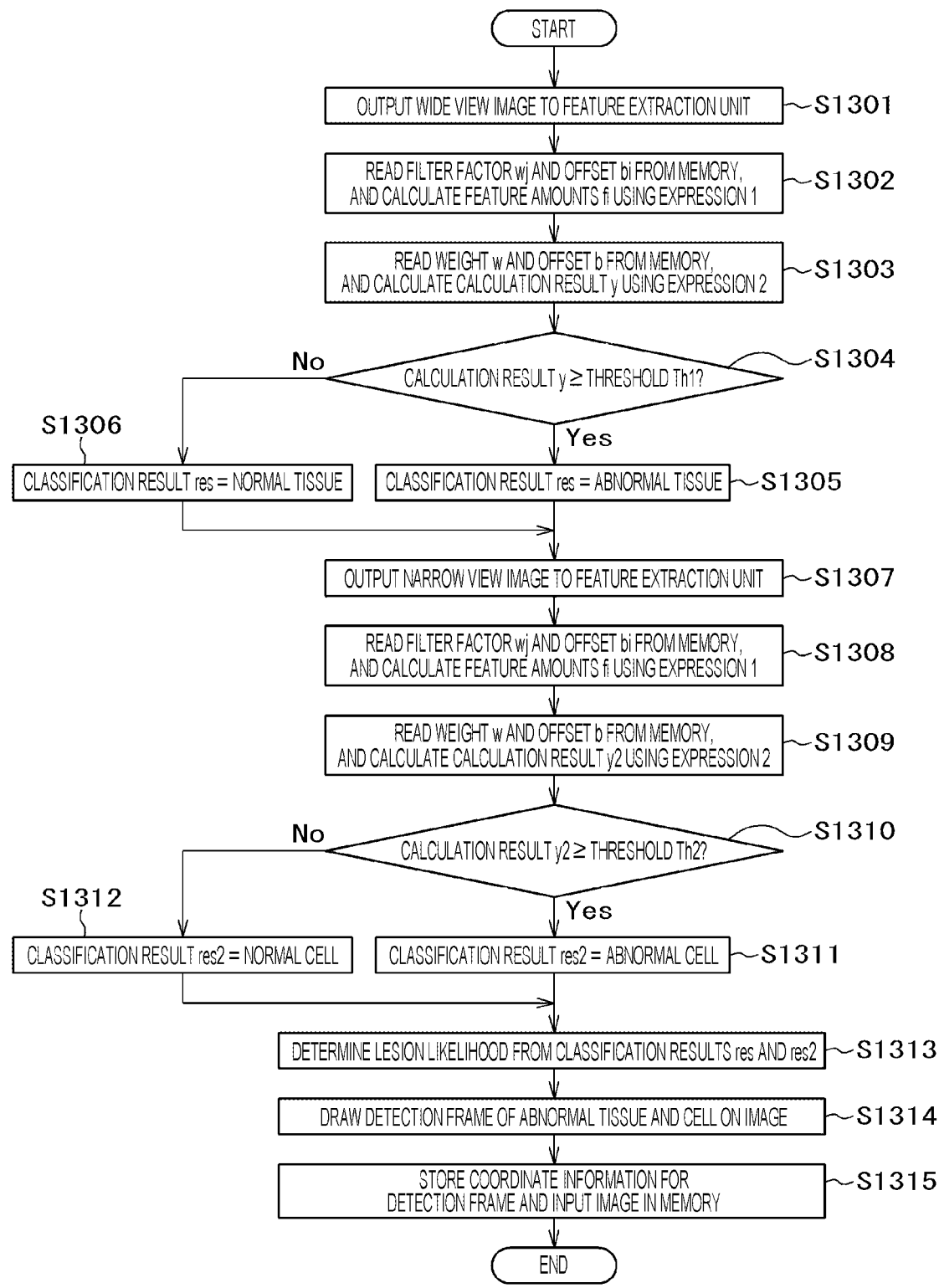
FIG. 13 is a flowchart for describing a whole operation of a diagnostic imaging assistance apparatus 1 in the first embodiment of the invention.

FIG. 13 is a flowchart for describing an operation of the diagnostic imaging assistance apparatus 1 according to the embodiment of the invention. In the following, the processing units (the input unit 10, the feature extraction unit 11, etc.) will be described as the operation subject, but the CPU 201 may be replaced as the operation subject and the processing units as programs.

(i) Step: S1301

The input unit 10 receives a determination-target wide view image (corresponding to the wide view image 310 of FIG. 3A), and outputs the input wide view image to the feature extraction unit 11.

(ii) Step: S1302

The feature extraction unit 11 reads the filter factor wj and the offset bi stored in the memory 90 in S1204 from the memory 90, and obtains the feature amount fi (601 to 60N of FIG. 6) of the tissue (5011 to 501N of FIG. 6) using the plurality of filters (4011 to 401N of FIG. 6) using the above Expression (Math. 1).

(iii) Step: S1303

The single view determination unit 12 reads the filter factor w and the offset b stored in the memory 90 in S1204 from the memory 90, and calculates a calculation result y by Expression (Math. 2).

(iv) Step: S1304

The single view determination unit 12 compares the calculated calculation result y with a threshold Th1, and classifies whether the wide view image is the normal tissue or the abnormal tissue (610 of FIG. 6). In other words, in the case of the calculation result y≥the threshold Th1, the image is classified into the abnormal tissue, and the process proceeds to step: S1305. On the other hand, in the case of the calculation result y<the threshold Th1, the image is classified into the normal tissue, and the process proceeds to step: S1306.

(v) Step: S1305

The single view determination unit 12 sets the abnormal tissue (for example, 1) to a classification result res.

(vi) Step: S1306

The single view determination unit 12 sets the normal tissue (for example, 0) to the classification result res.

(vii) Step: S1307

The narrow view image (corresponding to the narrow view image 320 of FIG. 3B) corresponding to the abnormal place of the detected tissue is acquired, and the narrow view image is output to the feature extraction unit 11.

(viii) Step: S1308

The feature extraction unit 11 reads the filter factor wj and the offset bi stored in the memory 90 in S1204 from the memory 90, and obtains the feature amount fi (9211 to 921N of FIG. 9) of the cell (8021 to 802N of FIG. 9) using the plurality of filters (7011 to 701N of FIG. 9) using the above Expression (Math. 1).

(ix) Step: S1309

The single view determination unit 12 reads the filter factor w and the offset b stored in the memory 90 in S1204 from the memory 90, and calculates a calculation result y2 by Expression (Math. 2).

(x) Step: S1310

The single view determination unit 12 compares the calculated calculation result y2 with a threshold Th2, and classifies whether the narrow view image is the normal cell or the abnormal cell (930 of FIG. 9). In other words, in the case of the calculation result y2≥the threshold Th2, the image is classified into the abnormal cell, and the process proceeds to step: S1311. On the other hand, in the case of the calculation result y2<the threshold Th2, the image is classified into the normal cell, and the process proceeds to step: S1312.

(xi) Step: S1311

The single view determination unit 12 sets the abnormal cell (for example, 1) to a classification result res2.

(xii) Step: S1312

The single view determination unit 12 sets the normal cell (for example, 0) to a classification result res2.

(xiii) Step: S1313

The multiple view determination unit 13 combines the classification result res of the wide view and the classification result res2 of the narrow view, and classifies the lesion likelihood. For example, the classification result res of the breast is set to a result such as the cribriform type, the comedo type, the solid type, and the papillary type. In addition, the classification result res2 is set to a result such as normality, benignancy, and malignancy. Therefore, the lesion type (for example, malignancy and a cribriform type) or the lesion likelihood (y=0.89: value range (0 to 1), y2=0.85: value range (0 to 1)) may be obtained by combining the classification results res and res2 and the calculation results y and y2.

(xiv) Step: S1314

The drawing unit 14 draws and displays the detection frames 1010 and 1110 indicating the place 1001 suspected of the abnormal tissue and the place 1101 suspected of the abnormal cell on the target images 1000 and 1100 in a case where the image is classified into the abnormal tissue and the abnormal cell as illustrated in FIGS. 10 and 11. The drawing unit 14 does not draw the detection frame on the target images 1000 and 1100 in a case where the image is classified into the normal tissue and the normal cell.

Figure 22:
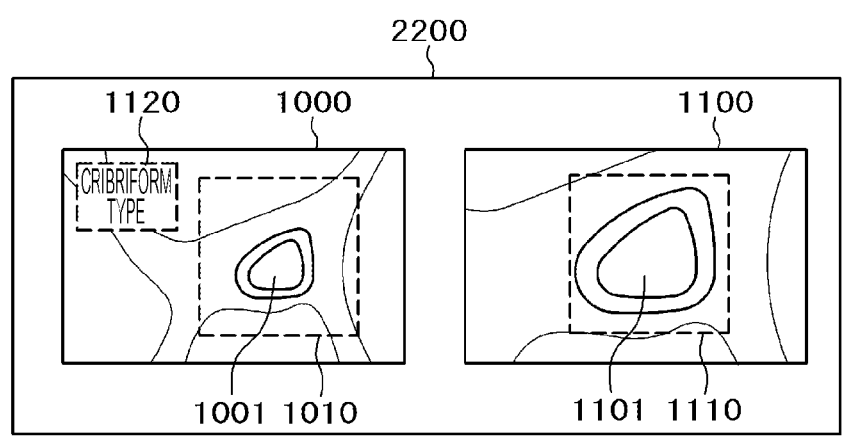
FIG. 22 is a front view of an image illustrating a state where the wide view image and the narrow view image are displayed on the same screen according to the first embodiment of the invention.

FIG. 22 illustrates an example in which the wide view image 1000 and the narrow view image 1100 are displayed on the same screen 2200 side by side. In the example illustrated in FIG. 22, the detection frame 1010 is displayed in a region surrounding the place 1001 suspected of the abnormal tissue in the wide view image 1000. The determination result of the lesion likelihood is displayed in the determination result display region 1120. The detection frame 1110 is displayed in a region surrounding the place 1101 suspected of the abnormal cell in the narrow view image 1100.

In this way, the detailed image of the lesion-causing place and the ambient state of the lesion-causing place can be compared on the same screen by displaying the wide view image 1000 and the narrow view image 1100 side by side on the same screen 2200. The lesion likelihood can be efficiently determined by comparing with a case where the image is switched and displayed.

(xv) Step: S1315

The recording unit 15 stores coordinate information for drawing the detection frame on the input target image by the drawing unit 14 and the target image in the memory 90 (corresponding to the storage device 203).

According to the first embodiment, the deformed degree of the tissue and the cell is learned using the feature amount of the tissue and the cell obtained by the plurality of filters. The weight, the filter factor, and the offset are calculated to create the identifier to classify the normal tissue or the abnormal tissue and the identifier to classify the normal cell or the abnormal cell. Therefore, an erroneous detection and an excessive detection can be suppressed with respect to the lesion detection, and the normal tissue or the abnormal tissue, and the normal cell or the abnormal cell can be classified from the image.

In addition, the tissue/cell is classified using the classification result of the identifier with respect to the images having different predetermined views. Therefore, it is possible to classify the lesion likelihood of the abnormal tissue or cell (example: cancer) according to the progress degree of the abnormal tissue or cell (example: cancer).

In addition, the lesion of the regions having different views are classified instead of determining the lesion likelihood of only one view. Therefore, it is possible to suppress erroneous detection in the classification.

In addition, the feature of the abnormal cell of the narrow view is selectively analyzed with respect to the detected abnormal tissue of the wide view. Therefore, it is possible to classify the lesion likelihood of the cell from the abnormal place of the tissue.

According to this embodiment, the diagnostic imaging assistance apparatus 1 performs a process of obtaining the feature amount of the tissue and the cell using the plurality of filters and performing the machine learning on the deformed degree of the tissue and the cell using the obtained feature amount, a process of classifying the normal tissue or the abnormal tissue using the identifier obtained by the machine learning, a process of classifying the normal cell or the abnormal cell from the narrow view image from the abnormal place of the wide view image, and a process of combining the classification results of the plurality of predetermined views to classify the lesion likelihood of the abnormal tissue or cell (example: cancer) according to the progress degree of the abnormal tissue or cell (example: cancer).

More specifically, as shown in Expression (Math. 1), the feature amount of the tissue and the cell is obtained using the plurality of filters. As shown in Expression (Math. 2), the machine learning is performed on the deformed degree of the tissue and the cell to determine the abnormal tissue or cell as the abnormal tissue or cell, so that the weight of the identifier, the filter factor, and the offset are calculated.

Then, using the weight of the identifier, the filter factor, and the offset obtained by the machine learning, the tissue and the cell in the determination-target input image can be classified to the normal tissue or the abnormal tissue from the wide view image, or the normal cell or the abnormal cell from the narrow view image.

Further, the lesion likelihood of the abnormal tissue or cell (example: cancer) according to the progress degree of the abnormal tissue or cell (example: cancer) is classified by combining the classification results of the plurality of predetermined views. Therefore, it is possible to display the classification results according to the progress degree of the abnormal tissue or cell (example: cancer).

Second Embodiment

A diagnostic imaging assistance apparatus 1-1 according to a second embodiment of the invention (see FIG. 1) includes the same configurations and functions as those of the diagnostic imaging assistance apparatus 1 described using FIG. 1 in the first embodiment, but the operation of a single view determination unit 12-1 is different from the first embodiment. Therefore, herein, the different process configurations will be described using FIGS. 14A and 14B, and the entire processing flow different from FIG. 13 will be described using FIG. 15.

Figure 14A:
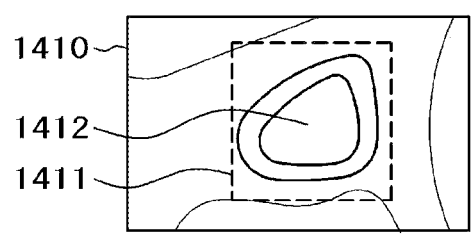
FIG. 14A is a diagram illustrating the narrow view image of a state where the detection frame is displayed in a region surrounding an abnormal place of a detected cell on the narrow view image in a second embodiment of the invention.
Figure 14B:
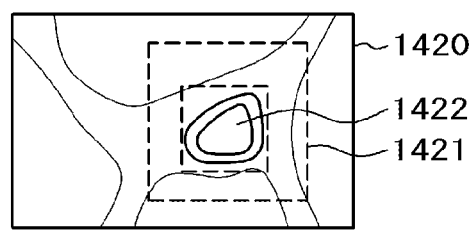
FIG. 14B is a diagram illustrating the wide view image of a state where the detection frame is displayed in a region surrounding an abnormal place of a detected tissue on the wide view image in a second embodiment of the invention.

The diagnostic imaging assistance apparatus 1-1 in this embodiment detects the normality/abnormality and the abnormal place of a cell 1412 in a region surrounded by a detection frame 1411 of a narrow view image 1410 as illustrated in FIG. 14A. A wide view image 1420 illustrated in FIG. 14B is obtained with respect to the detected abnormal place. The normality/abnormality and the abnormal place of a tissue 1422 in a region surrounded by a detection frame 1421 of the wide view image 1420 are detected. The lesion likelihood is determined from the normality/abnormality and the abnormal place which are detected.

In the diagnostic imaging assistance apparatus 1-1 according to this embodiment, the single view determination unit 12-1 determines the representative pixel of the abnormal place in the narrow view image 1410 and creates a low resolution image corresponding to the representative pixel, or retrieves a low magnification image corresponding to the representative pixel to acquire the wide view image 1420.

Figure 21:
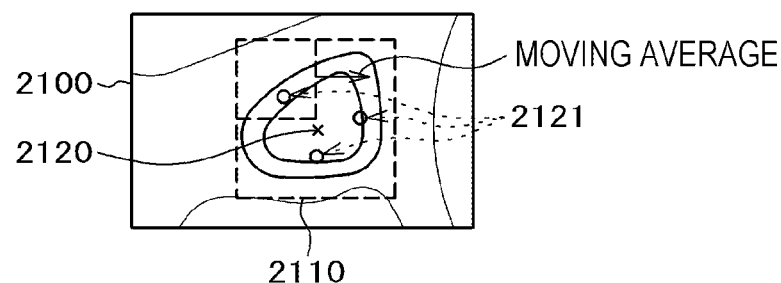
FIG. 21 is a diagram illustrating an image for describing the center of a distribution of a lesion likelihood in the narrow view image of the single view determination unit 12 in the first embodiment of the invention.

The representative pixel is an arbitrary pixel in an abnormal place in a region surrounded by the detection frame 1411 in the narrow view image 1410, a pixel having a maximum lesion likelihood, or a pixel at the center of the distribution of the lesion likelihood. For example, the distribution center may be a pixel 2120 in which the calculation result of a moving average of the distribution of a lesion-causing place 2121 in the region surrounded by a detection frame 2110 of a narrow view image 2100 illustrated in FIG. 21 is maximum.

<Configuration and Operation of Units>

Hereinafter, the configuration and the operation of each element different from FIG. 1 will be described.

(ii) Single View Determination 112-1

The single view determination 112-1 classifies whether the cell in the input tissue/cell image is normal or abnormal by Expression (Math. 2) using each feature amount fi from the plurality of filters C1:7011 to CN:701N which relate to the shape of arbitrary cell obtained by the feature extraction 111 as illustrated in FIG. 9. Similarly, the single view determination 112-1 classifies whether the tissue in the input tissue/cell image is normal or abnormal by Expression (Math. 2) using each feature amount fi from the plurality of filters T1:4011 to TN:401N which relate to the shapes of arbitrary tissues 5011 to 501N obtained by the feature extraction 111 as illustrated in FIG. 6.

<Hardware Configuration of Diagnostic Imaging Assistance Apparatus>

An exemplary hardware configuration of the diagnostic imaging assistance apparatus 1-1 according to this embodiment is the same as that described using FIG. 2 in the first embodiment except the single view determination unit 12-1. The single view determination unit 12-1 in this embodiment performs the function of the single view determination 112-1.

Figure 15:
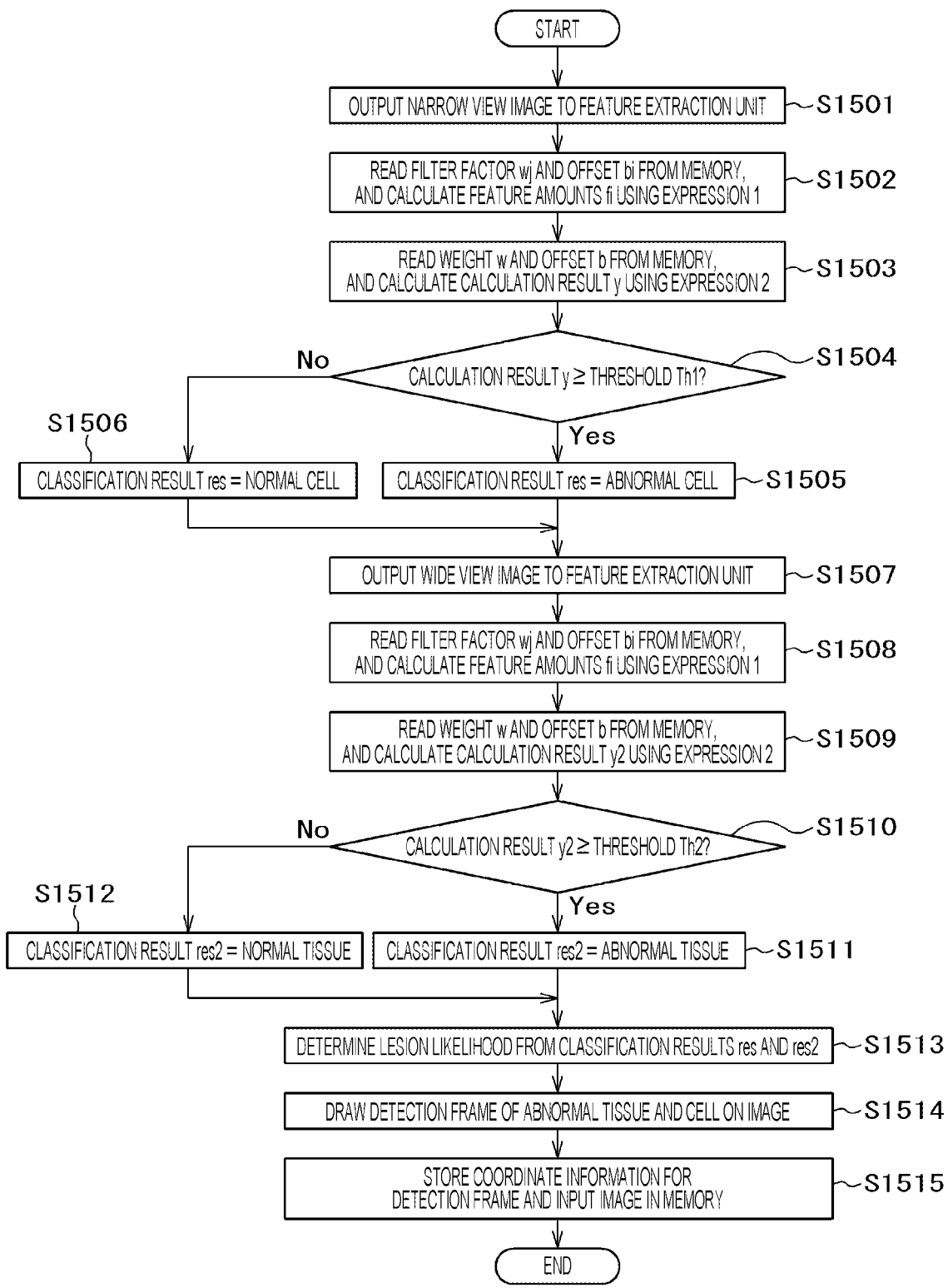
FIG. 15 is a flowchart for describing a whole operation of a diagnostic imaging assistance apparatus 1-1 according to the second embodiment of the invention.

FIG. 15 is a flowchart for describing an operation of the diagnostic imaging assistance apparatus 1-1 according to this embodiment. In the following, the processing units (the input unit 10, the feature extraction unit 11, etc.) will be described as the operation subject, but the CPU 201 may be replaced as the operation subject and the processing units as programs.

(i) Step: S1501

The input unit 10 receives the determination-target narrow view image (corresponding to the image 1410 of FIG. 14A), and outputs the input image to the feature extraction unit 11.

(ii) Step: S1502

The feature extraction unit 11 reads the filter factor wj and the offset bi stored in the memory 90 in S1204 from the memory 90, and obtains the feature amount fi (corresponding to 9211 to 921N of FIG. 9) of the cell (corresponding to 8021 to 802N of FIG. 9) using the plurality of filters (corresponding to 7011 to 701N of FIG. 9) using the above Expression (Math. 1).

(iii) Step: S1503

The single view determination unit 12-1 reads the filter factor w and the offset b stored in the memory 90 in S1204 from the memory 90, and calculates a calculation result y by Expression (Math. 2).

(iv) Step: S1504

The single view determination unit 12-1 compares the calculated calculation result y with a threshold Th1, and classifies whether the narrow view image is the normal cell or the abnormal cell. In other words, in the case of the calculation result y the threshold Th1, the image is classified into the abnormal cell, and the process proceeds to step: S1505. On the other hand, in the case of the calculation result y<the threshold Th1, the image is classified into the normal cell, and the process proceeds to step: S1506.

(v) Step: S1505

The single view determination unit 12-1 sets the abnormal cell (for example, 1) to a classification result res.

(vi) Step: S1506

The single view determination unit 12-1 sets the normal cell (for example, 0) to a classification result res.

(vii) Step: S1507

The wide view image (corresponding to the image 1420 of FIG. 14B) corresponding to the abnormal place of the detected cell is acquired, and the wide view image is output to the feature extraction unit 11.

(viii) Step: S1508

The feature extraction unit 11 reads the filter factor wj and the offset bi stored in the memory 90 in S1204 from the memory 90, and obtains the feature amount fi (corresponding to 601 to 60N of FIG. 6) of the tissue (corresponding to 5011 to 501N of FIG. 6) using the plurality of filters (corresponding to 4011 to 401N of FIG. 6) using the above Expression (Math. 1).

(ix) Step: S1509

The single view determination unit 12-1 reads the filter factor w and the offset b stored in the memory 90 in S1204 from the memory 90, and calculates a calculation result y2 by Expression (Math. 2).

(x) Step 1510

The single view determination unit 12-1 compares the calculated calculation result y2 with a threshold Th2, and classifies whether the wide view image is the normal tissue or the abnormal tissue. In other words, in the case of the calculation result y2 the threshold Th2, the image is classified into the abnormal tissue, and the process proceeds to step: S1511. On the other hand, in the case of the calculation result y2<the threshold Th2, the image is classified into the normal tissue, and the process proceeds to step: S1512.

(xi) Step: S1511

The single view determination unit 12-1 sets the abnormal tissue (for example, 1) to a classification result res2.

(xii) Step: S1512

The single view determination unit 12-1 sets the normal tissue (for example, 0) to a classification result res2.

(xiii) Step: S1513

The multiple view determination unit 13 combines the classification result res of the narrow view and the classification result res2 of the wide view, and classifies the lesion likelihood. For example, in the case of the breast, the classification result res is set to a result such as normality, benignancy, and malignancy. In addition, the classification result res2 is set to a result such as the cribriform type, the comedo type, the solid type, and the papillary type. Therefore, the lesion type (for example, malignancy and a cribriform type) or the lesion likelihood (y=0.85: value range (0 to 1), y2=0.89: value range (0 to 1)) may be obtained by combining the classification results res and res2 and the calculation results y and y2.

(xiv) Step: S1514

The drawing unit 14 draws and displays the detection frames 1010 and 1110 indicating the place 1001 suspected of the abnormal tissue and the place 1101 suspected of the abnormal cell on the target image 1000 or 1100 in a case where the image is classified into the abnormal tissue and the abnormal cell as illustrated in FIGS. 10 and 11. The drawing unit 14 does not draw the detection frame on the target image 1000 or 1100 in a case where the image is classified into the normal tissue and the normal cell.

In addition, similarly to the case of the first embodiment, as illustrated in FIG. 22, the wide view image 1000 and the narrow view image 1100 can be displayed on the same screen 2200 side by side.

(xv) Step: S1515

The recording unit 15 stores coordinate information for drawing the detection frame on the input target image by the drawing unit 14 and the target image in the memory 90 (corresponding to the storage device 203).

According to the second embodiment, the deformed degree of the tissue and the cell is learned using the feature amount of the tissue and the cell obtained by the plurality of filters. The weight, the filter factor, and the offset are calculated to create the identifier to classify the normal tissue or the abnormal tissue and the identifier to classify the normal cell or the abnormal cell. Therefore, an erroneous detection and an excessive detection can be suppressed with respect to the lesion detection, and the normal tissue or the abnormal tissue, and the normal cell or the abnormal cell can be classified from the image.

In addition, the tissue/cell is classified using the classification result of the predetermined identifier. Therefore, it is possible to classify the lesion likelihood of the abnormal tissue or cell (example: cancer) according to the progress degree of the abnormal tissue or cell (example: cancer).

In addition, the lesion of the regions having different views are classified instead of determining the lesion likelihood of only one view. Therefore, it is possible to suppress erroneous detection in the classification.

In addition, the feature of the abnormal tissue of the wide view is selectively analyzed with respect to the detected abnormal cell of the narrow view. Therefore, it is possible to classify the lesion likelihood of the tissue from the abnormal place of the cell.

According to this embodiment, the diagnostic imaging assistance apparatus 1-1 classifies whether the tissue and the cell in the determination-target input image are the normal cell or the abnormal cell from the narrow view image, classifies whether the tissue and the cell are the normal tissue or the abnormal tissue from the wide view image from the abnormal place of the narrow view image, and combines the classification results of the plurality of predetermined views to classify the lesion likelihood of the abnormal tissue or cell (example: cancer) corresponding to the progress degree of the abnormal tissue or cell (example: cancer). Therefore, it is possible to display the classification result according to the progress degree of the abnormal tissue or cell (example: cancer).

Third Embodiment

A diagnostic imaging assistance apparatus 1-2 according to a third embodiment of the invention (see FIG. 1) includes the same configurations and functions as those of the diagnostic imaging assistance apparatus 1 described using FIG. 1 in the first embodiment, but the process of a single view determination unit 112-2 is different from the first and second embodiments. Therefore, herein, the process different from that of the first and second embodiments, that is, the entire processing flow different from that of the first or second embodiment described in FIG. 13 or 15 will be described using FIG. 17.

Figure 16:
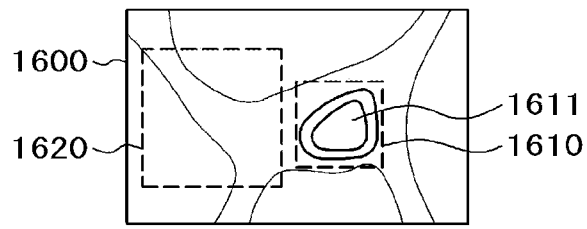
FIG. 16 is a diagram illustrating an image of a state where a narrow view region and a wide view region according to the third embodiment of the invention are displayed on the same image.

In the diagnostic imaging assistance apparatus 1-2 according to this third embodiment, as illustrated in FIG. 16, the normality/abnormality and the abnormal place of the cell are detected from the narrow view image of the same image, the normality/abnormality and the abnormal place of the tissue from the wide view image of the same image are detected, and the lesion likelihood is determined from the normality/abnormality and the abnormal place which are detected. In the diagnostic imaging assistance apparatus 1-2 according to this embodiment, two images having different views (the size of the region) are acquired from the same image in the single view determination 112-2.

<Configuration and Operation of Units>

Hereinafter, the configuration and the operation of each element different from FIG. 1 will be described.

(ii) Single View Determination 112-2

With respect to a narrow view image 1610 in a histopathological image 1600 illustrated in FIG. 16, the single view determination 112-2 classifies whether the cell in the input tissue/cell image is normal or abnormal by Expression (Math. 2) using each feature amount fi from the plurality of filters C1:7011 to CN:701N which relate to the shape of arbitrary cell 1611 obtained by the feature extraction 111 as illustrated in FIG. 9.

Similarly, with respect to a wide view image 1620 in a histopathological image 1600 illustrated in FIG. 16, the single view determination 112-2 classifies whether the tissue in the input tissue/cell image is normal or abnormal by Expression (Math. 2) using each feature amount fi from the plurality of filters T1:4011 to TN:401N which relate to the shape of arbitrary tissue obtained by the feature extraction 111 as illustrated in FIG. 6.

<Hardware Configuration of Diagnostic Imaging Assistance Apparatus>

An exemplary hardware configuration of the diagnostic imaging assistance apparatus 1-2 according to the embodiment of the invention is similar to FIG. 2.

Figure 17:
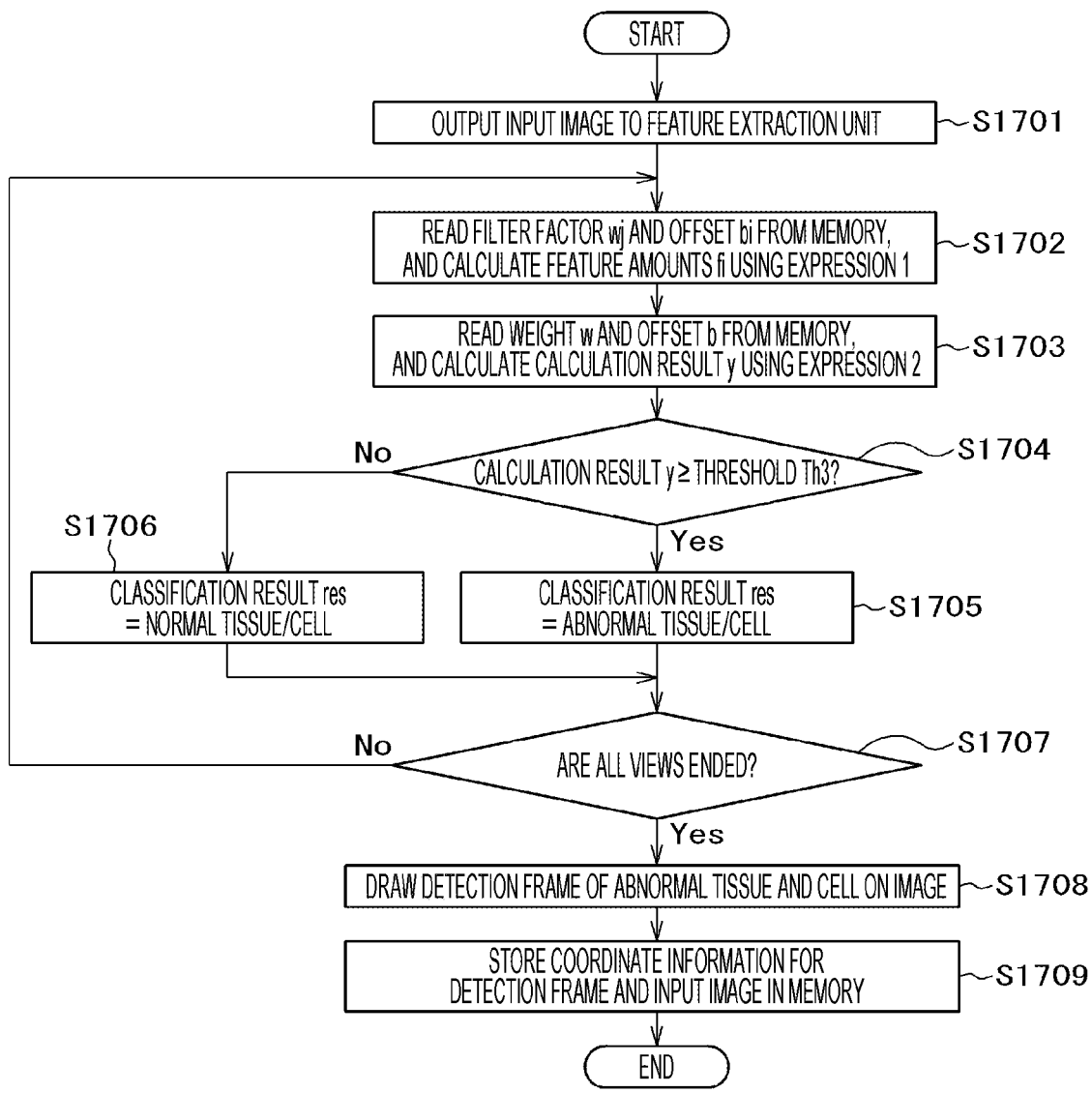
FIG. 17 is a flowchart for describing a whole operation of a diagnostic imaging assistance apparatus 1-2 according to the third embodiment of the invention.

FIG. 17 is a flowchart for describing an operation of the diagnostic imaging assistance apparatus 1-2 according to the embodiment of the invention. In the following, the processing units (the input unit 10, the feature extraction unit 11, etc.) will be described as the operation subject, but the CPU 201 may be replaced as the operation subject and the processing units as programs.

(i) Step: S1701

The input unit 10 receives the determination-target narrow view image and the wide view image, and outputs the input image to the feature extraction unit 11.

(ii) Step: S1702

The feature extraction unit 11 reads the filter factor wj and the offset bi from the memory 90, and obtains the feature amount fi of the cell and the tissue using the plurality of filters using Expression (Math. 1).

(iii) Step: S1703

A single view determination unit 12-2 reads the filter factor w and the offset b from the memory 90, calculates the calculation results y by Expression 2, and classifies whether the narrow view image is the normal cell or the abnormal cell, or the wide view image is the normal tissue or the abnormal tissue.

(iv) Step: S1704

The single view determination unit 12-2 compares the calculated calculation result y and a threshold Th3. In other words, in the case of calculation result y threshold Th3, the process proceeds to step: S1705. On the other hand, in the case of calculation result y<threshold Th3, the process proceeds to step: S1706.

(v) Step: S1705

The single view determination unit 12-2 sets the abnormal cell (for example, 1) or the abnormal tissue (for example, 1) to the classification result res.

(vi) Step: S1706

The single view determination unit 12-2 sets the normal cell (for example, 0) or the normal tissue (for example, 0) to the classification result res.

(vii) Step: S1707

The multiple view determination unit 13 repeatedly performs steps: S1702 to S1706 to perform the single view determination 112-2 in the single view determination unit 12-2 with respect to all the predetermined views. With the process from steps: S1702 to S1706 repeatedly performed, it is possible to determine whether the image is the normal cell or the abnormal cell, and the normal tissue or the abnormal tissue with respect to all the predetermined views.

The multiple view determination unit 13 combines the classification result res of the narrow view and the classification result res of the wide view, and classifies the lesion likelihood. For example, the classification result res of the wide view of the breast is set to a result such as the cribriform type, the comedo type, the solid type, and the papillary type. In addition, the classification result res in the narrow view is set to a result such as normality, benignancy, and malignancy.

Therefore, the type of lesion (for example, malignancy and a cribriform type) and the lesion likelihood (the calculation result y in the wide view=0.89: value range (0 to 1), the calculation result y in the narrow view=0.85: value range (0 to 1)) can be obtained by combing the classification result res and the calculation result y in the wide view and the classification result res and the calculation result y in the narrow view.

(viii) Step: S1708

The drawing unit 14 draws and displays the detection frame indicating the abnormal tissue and the abnormal cell as illustrated in FIGS. 10 and 11 in a case where the image is classified into the abnormal tissue and the abnormal cell. The drawing unit 14 does not draw the detection frame on the image in a case where the image is classified into the normal tissue and the normal cell.

In addition, similarly to the first and second embodiments, as illustrated in FIG. 22, the wide view image 1000 and the narrow view image 1100 can be displayed on the same screen 2200 side by side.

(ix) Step: S1709

The recording unit 15 stores coordinate information for drawing the detection frame on the input target image by the drawing unit 14 and the target image in the memory 90 (corresponding to the storage device 203).

According to the third embodiment, the deformed degree of the tissue and the cell is learned using the feature amount of the tissue and the cell obtained by the plurality of filters. The weight, the filter factor, and the offset are calculated to create the identifier to classify the normal tissue or the abnormal tissue and the identifier to classify the normal cell or the abnormal cell. Therefore, an erroneous detection and an excessive detection can be suppressed with respect to the lesion detection, and the normal tissue or the abnormal tissue, and the normal cell or the abnormal cell can be classified from the image.

In addition, the tissue/cell is classified using the classification result of the predetermined identifier. Therefore, it is possible to classify the lesion likelihood of the abnormal tissue or cell (example: cancer) according to the progress degree of the abnormal tissue or cell (example: cancer).

In addition, the lesion of the regions having different views are classified instead of determining the lesion likelihood of only one view. Therefore, it is possible to suppress erroneous detection in the classification.

In addition, the presence/absence of the abnormal cell is detected with respect to the narrow view in the same image, and the presence/absence of the abnormal tissue is detected with respect to the wide view in the same image. Therefore, the types of lesions can be detected, so that the detection omission can be suppressed.

According to this embodiment, the diagnostic imaging assistance apparatus 1-2 classifies whether the tissue and the cell in the determination-target input image are the normal cell or the abnormal cell from the narrow view image in the same image, classifies whether the tissue and the cell are the normal tissue or the abnormal tissue from the wide view image in the same image, and combines the classification results of the plurality of predetermined views to classify the lesion likelihood of the abnormal tissue or cell (example: cancer) corresponding to the progress degree of the abnormal tissue or cell (example: cancer). Therefore, it is possible to display the classification result according to the progress degree of the abnormal tissue or cell (example: cancer).

Fourth Embodiment

Figure 18:
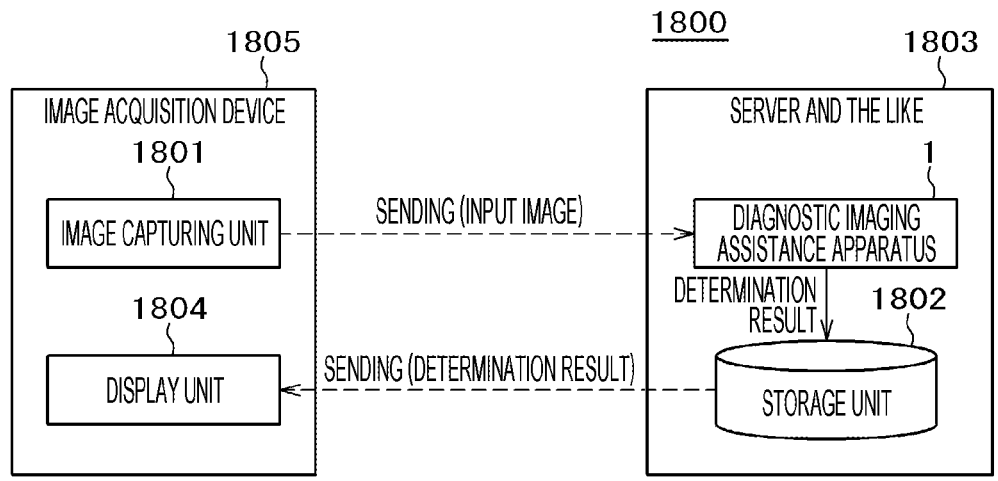
FIG. 18 is a block diagram illustrating an outline of a remote diagnostic assistance system mounted with the diagnostic imaging assistance apparatus according to a fourth embodiment of the invention.

FIG. 18 is a functional block diagram illustrating a configuration of a remote diagnostic assistance system 1800 according to a fourth embodiment of the invention. The remote diagnostic assistance system 1800 according to this embodiment includes a server 1803 which includes the diagnostic imaging assistance apparatus 1, 1-1, or 1-2 (in FIG. 18, simply displayed as the diagnostic imaging assistance apparatus 1), and an image acquisition device 1805 which includes an image capturing unit 1801 to capture image data.

The image acquisition device 1805 transmits (sends) the image data to the server 1803. The server 1803 stores the images of the tissue and the cell determined by processing the received image data (input image) using the diagnostic imaging assistance apparatus 1, 1-1, or 1-2 (hereinafter, simply referred to as the diagnostic imaging assistance apparatus 1) described in the first to third embodiments and the determination result in the memory of a storage unit 1802, and transmits the images and the determination result to the image acquisition device 1805. The image acquisition device 1805 is configured to display the images of the tissue and the cell determined by the processing using the diagnostic imaging assistance apparatus 1 which is received from the server 1803 and the determination result on a display unit 1804.

The server 1803 includes the diagnostic imaging assistance apparatus 1 which includes a processor to execute various types of programs to process the target image, and the storage unit 1802 which includes a memory to store the image processing result.

Then, the diagnostic imaging assistance apparatus 1 equipped with the processor performs a process of inputting an image obtained by capturing the tissue and the cell, a process of outputting the feature amount of the wide view and the narrow view from the plurality of target images, a process of classifying the presence/absence of the lesion and a probability of the lesion for the target images having a plurality of different views using the plurality of feature amounts, and a process of determining the presence/absence of the lesion and the probability of the lesion using the plurality of classification results.

On the other hand, the image acquisition device 1805 transmits the image data to the server 1803. The server 1803 stores the images of the tissue and the cell determined by processing the received image data using the diagnostic imaging assistance apparatus 1 and the determination result in the memory of the storage unit 1802, and transmits the images and the determination result to the image acquisition device 1805. The image acquisition device 1805 which receives the image and the determination result displays the images of the tissue and the cell which is received and determined and the determination result on the display unit 1804.

The image acquisition device 1805 is a device such as a personal computer in which a virtual slide device and a camera are mounted, and includes the image capturing unit 1801 which captures the image data and the display unit 1804 to display the determination result transmitted from the server 1803. Further, while not illustrated, the image acquisition device 1805 includes a communication device which transmits the image data to the server 1803, and receives data transmitted from the server 1803.

The server 1803 includes the diagnostic imaging assistance apparatus 1 and the storage unit 1802 which stores the determination result output from the diagnostic imaging assistance apparatus 1 with respect to the image data transmitted from the image acquisition device 1805. Further, while not illustrated, the server 1803 includes a communication device which receives the image data transmitted from the image acquisition device 1805, and transmits the determination result data to the image acquisition device 1805.

The diagnostic imaging assistance apparatus 1 classifies the presence/absence of the abnormal tissue and the abnormal cell (example: cancer) with respect to the tissue and the cell in the image data captured by the image capturing unit 1801. In addition, using the classification result using the identifiers of the plurality of predetermined views, the lesion likelihood of the abnormal tissue and the abnormal cell is classified according to the progress degree of the abnormal tissue and the abnormal cell (example: cancer). The display unit 1804 displays the classification result sent from the server 1803 to the display screen of the image acquisition device 1805.

Examples of the image acquisition device 1805 may include a reproducing medical device which includes an imaging unit, a culture device of iPS cells, MRI, or an ultrasonic image capturing device.

According to this embodiment, it is possible to provide a remote diagnostic assistance system which classifies the tissue and the cell sent from facilities installed at different places as the normal tissue or the abnormal tissue and the normal cell or the abnormal cell, sends the classification result to the facilities at different places, and displays the classification result in the display units of the image acquisition devices of the facilities.

Fifth Embodiment

Figure 19:
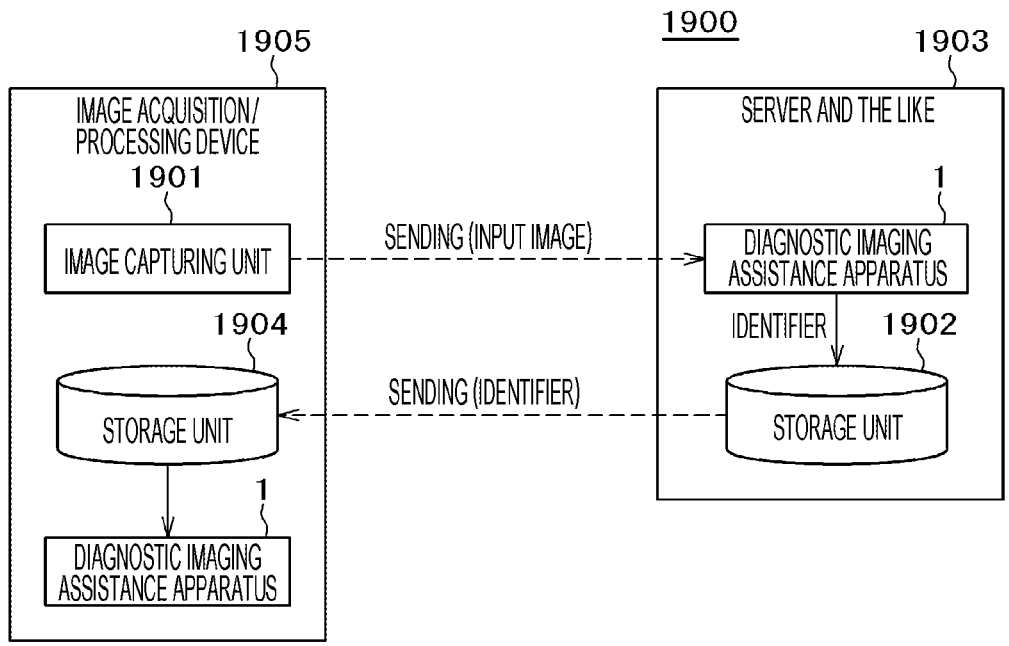
FIG. 19 is a block diagram illustrating an outline of a network entrusting service provision system mounted with the diagnostic imaging assistance apparatus according to a fifth embodiment of the invention.

FIG. 19 is a functional block diagram illustrating a configuration of a network entrusting service provision system 1900 according to a fifth embodiment of the invention. The network entrusting service provision system 1900 includes the server 1903 and an image acquisition/processing device 1905.

The network entrusting service provision system 1900 according to this embodiment includes the image acquisition/processing device 1905 which includes an image capturing unit 1901 to capture the image data, and a server 1903 which includes the diagnostic imaging assistance apparatus 1, 1-1, or 1-2 (in FIG. 19, simply displayed as the diagnostic imaging assistance apparatus 1) described in the first to third embodiments. The image acquisition/processing device 1905 transmits (sends) the image data to the server 1903. The server 1903 stores the images of the tissue and the cell determined by processing the received image data using the diagnostic imaging assistance apparatus 1, 1-1, or 1-2 (hereinafter, simply referred to as the diagnostic imaging assistance apparatus 1) and the identifier in the memory, and transmits the identifier to the image acquisition/processing device 1905. The image acquisition/processing device 1905 stores the identifier received from the server 1903. The diagnostic imaging assistance apparatus 1 in the image acquisition/processing device 1905 is configured to determine the image of the other tissues and cells using the identifier, and display the determination result on the display device.

The image acquisition/processing device 1905 is, for example, a personal computer in which a virtual slide device and a camera are mounted, and includes the image capturing unit 1901 to capture the image data, a storage unit 1904 to store the identifier sent from the server 1903, and the diagnostic imaging assistance apparatus 1 which reads the identifier sent from the server 1903 and classifies whether the tissue and the cell in an image newly captured by the image capturing unit 1901 of the image acquisition/processing device 1905 are the normal tissue or the abnormal tissue and the normal cell or the abnormal cell. Further, while not illustrated, the image acquisition/processing device 1905 includes a communication device which transmits the image data to the server 1903, and receives data transmitted from the server 1903.

The server 1903 includes the diagnostic imaging assistance apparatus 1 which performs the image processing according to the first, second, and third embodiments of the invention on the image data sent from the image acquisition/processing device 1905, and a storage unit 1902 which stores the identifier output from the diagnostic imaging assistance apparatus 1. Further, while not illustrated, the server 1903 includes a communication device which receives the image data transmitted from the image acquisition/processing device 1905, and transmits the identifier to the image acquisition/processing device 1905.

The diagnostic imaging assistance apparatus 1 performs the machine learning on the tissue and the cell in the image data captured by the image capturing unit 1901 such that the normal tissue or cell is determined as a normal tissue or cell, or the abnormal tissue or cell is determined as an abnormal tissue or cell, and creates the identifiers which are suitable to the images of the facilities at different places.

The storage unit 1904 stores the identifier sent from the server 1903.

The diagnostic imaging assistance apparatus 1 in the image acquisition/processing device 1905 reads the identifier from the storage unit 1904, classifies whether the tissue and the cell in an image newly captured by the image capturing unit 1901 of the image acquisition/processing device 1905 is the normal tissue or the abnormal tissue and the normal cell or the abnormal cell using the identifier, and displays the classification result on the display screen of the output device 204 (see FIG. 2) of the diagnostic imaging assistance apparatus 1.

Examples of the image acquisition/processing device 1905 may include a reproducing medical device which includes an imaging unit, a culture device of iPS cells, MRI, or an ultrasonic image capturing device.

According to the fifth embodiment, it is possible to provide a network entrusting service provision system which performs the machine learning on the tissue and the cell in the images sent from the facilities at different places to classify the normal tissue or cell as a normal tissue or cell or the abnormal tissue or cell as an abnormal tissue or cell so as to create the identifier, sends the identifier to the facilities at different places, reads the identifier by the image acquisition device in the facility, and classifies whether the tissue and the cell in the newly captured image is the normal tissue or the abnormal tissue and the normal cell or the abnormal cell.

The first to fifth embodiments described above may be modified as follows.

In the feature extraction unit 11 and the learning unit 16, the plurality of feature amounts are obtained using the filter illustrated in FIGS. 4 and 7. However, other feature amount such as HOG may be used to achieve the similar effect.

In the single view determination unit 12, the deformed degree of the tissue and the cell has been machine-learned using the logistic regression. However, a linear regression and a Poisson regression may be used to achieve the similar effect.

The invention may be realized by a software program code to realize the functions of the embodiments. In this case, a storage medium for storing the program code is provided in a system or a device. A computer (CPU or MPU) of the system or the device reads out the program code stored in the storage medium. In this case, the program code itself read out of the recording medium is used to realize the functions of the above embodiments. The program code itself and the storage medium storing the program code is configured in the invention. As a storage medium to supply such a program code, for example, there are a flexible disk, a CD-ROM, a DVD-ROM, a hard disk, an optical disk, a magneto-optical disk, a CD-R, a magnetic tape, a nonvolatile memory card, and a ROM.

In addition, on the basis of a command of the program code, some or all of the actual processes may be performed by an OS (operating system) running on a computer, and the functions of the embodiments described above may be realized by the process. Further, after the program code read out of the storage medium is written in the memory on the computer, the CPU of the computer may perform some or all of the actual processes on the basis of the command of the program code, and the functions of the embodiments described above may be realized by the process.

Further, the software program code for realizing the functions of the embodiments is distributed through a network to be stored in a storage unit such as a hard disk and a memory of the system or the device or a storage medium such as CD-RW and CD-R. At the time of operation, the computer (or CPU and MPU) of the system or the device may read out and perform the program code stored in the storage unit or the storage medium.

In addition, the process and the technology described herein are not limited to a specific device in principle, and may be applied in any combination according to components. Further, various types of general-purpose devices may be used according to the method described herein. In some cases, it may be beneficial to establish a dedicated device to perform the steps of the method described herein.

In addition, the invention may be implemented in various forms by appropriately combining the plurality of components disclosed in the embodiments. For example, some of the components may be removed from the components of the embodiments. Further, the components of different embodiments may be appropriately combined. The invention has been described in relation to the specific examples which are not intended to limit the invention in all viewpoints but only for explanation. A person skilled in the art may understand that a number of combinations of software, hardware, and firmware may be made to implement the invention. For example, the above-described software may be embedded by a wide program such as assembler, C/C++, perl, Shell, PHP, Java (registered trademark) or a script language.

Further, in the above embodiments, only control lines and information lines considered to be necessary for explanation are illustrated, but not all the control lines and the information lines for a product are illustrated. All the configurations may be connected to each other.

In addition, persons who have common knowledge in the technical field to which the inventions pertains may consider other modifications of the invention from the specification and the embodiments of the invention. Various or components of the above-described embodiments may be used alone or in any combination.

REFERENCE SIGNS LIST

1, 1-1, 1-2 diagnostic imaging assistance apparatus
10 input unit
11 feature extraction unit
12 single view determination unit
13 multiple view determination unit
14 drawing unit
15 recording unit
16 learning unit
1800 remote diagnostic assistance system
1900 network entrusting service provision system

The invention claimed is:

1. A diagnostic imaging assistance apparatus comprising:
an input unit configured to receive wide view image data and narrow view image data in a same image as image data obtained by capturing a slice of a tissue or a cell of a diagnostic object;
a feature extraction unit configured to process the image data input to the input unit to extract a feature amount on an image of the tissue from the wide view image data and extract a feature amount on an image of the cell from the narrow view image data;
a single view determination unit configured to classify whether the tissue is normal or abnormal from the feature amount of the wide view image data extracted by the feature extraction unit, and classify whether the cell is normal or abnormal from the feature amount of the narrow view image data;

a multiple view determination unit configured to classify a lesion likelihood of the diagnostic object from a classification result of the wide view image data and a classification result of the narrow view image data classified by the single view determination unit;
a drawing unit configured to actualize a region containing the tissue or the cell classified as abnormal by the multiple view determination unit on the image data; and
a recording unit configured to store an image of which the region containing the tissue or the cell classified as abnormal is actualized by the drawing unit.

2. The diagnostic imaging assistance apparatus according to claim 1, further comprising a learning unit configured to create a first identifier to classify whether the tissue in the image data input to the input unit is a normal tissue or an abnormal tissue using the feature amount of the wide view image data of a slice of the tissue extracted by the feature extraction unit and a result obtained by classifying whether the tissue is normal or abnormal by the single view determination unit, and a second identifier to classify whether the cell in the image data input to the input unit is a normal cell or an abnormal cell using the feature amount of the narrow view image data of a slice of the cell extracted by the feature extraction unit and a result obtained by classifying whether the cell is normal or abnormal by the single view determination unit.

3. The diagnostic imaging assistance apparatus according to claim 1, wherein the single view determination unit calculates a deformed degree of the tissue from the feature amount of the wide view image data to classify whether the tissue is normal or abnormal, and calculates a deformed degree of the cell from the feature amount of the narrow view image data to classify whether the cell is normal or abnormal.

4. The diagnostic imaging assistance apparatus according to claim 1, wherein the drawing unit surrounds a region containing the tissue or the cell classified as abnormal by the multiple view determination unit with a frame on the image data to actualize the region containing the tissue or the cell.

5. The diagnostic imaging assistance apparatus according to claim 1, further comprising an output unit including a display screen, wherein the wide view image data and the narrow view image data in which a region containing the tissue or the cell classified as abnormal by the multiple view determination unit is actualized in the drawing unit are displayed on the display screen of the output unit side by side.

6. A diagnostic imaging assistance method comprising:
inputting wide view image data obtained by capturing a tissue of a diagnostic object to an input unit;
processing the wide view image data input to the input unit by a feature extraction unit to extract a feature amount on an image of the tissue;
classifying whether the tissue is normal or abnormal by a single view determination unit from the feature amount of the wide view image data extracted by the feature extraction unit;
inputting narrow view image data in a same image as the wide view containing a cell captured from the tissue classified as abnormal by the single view determination unit to the input unit, the narrow view image data and the wide view image data comprising image data;
processing the narrow view image data input to the input unit by a feature extraction unit to extract a feature amount on an image of the cell;
classifying whether the cell is normal or abnormal by the single view determination unit from the feature amount of the narrow view image data extracted by the feature extraction unit;
classifying a lesion likelihood of the diagnostic object by a multiple view determination unit from a classification result of the wide view image data and a classification result of the narrow view image data classified by the single view determination unit;
actualizing a region containing the tissue or the cell classified as abnormal by the single view determination unit on the image data in a drawing unit; and
storing the image data obtained by actualizing the region containing the tissue or the cell classified as abnormal in a recording unit.

7. The diagnostic imaging assistance method according to claim 6, wherein a learning unit creates a first identifier to classify whether the tissue in the image data input to the input unit is a normal tissue or an abnormal tissue using the feature amount of the wide view image data of a slice of the tissue extracted by the feature extraction unit and a result obtained by classifying whether the tissue is normal or abnormal by the single view determination unit, and a second identifier to classify whether the cell in the image data input to the input unit is a normal cell or an abnormal cell using the feature amount of the narrow view image data of a slice of the cell extracted by the feature extraction unit and a result obtained by classifying whether the cell is normal or abnormal by the single view determination unit.

8. The diagnostic imaging assistance method according to claim 6, wherein the single view determination unit calculates a deformed degree of the tissue from the feature amount of the wide view image data to classify whether the tissue is normal or abnormal, and calculates a deformed degree of the cell from the feature amount of the narrow view image data to classify whether the cell is normal or abnormal.

9. The diagnostic imaging assistance method according to claim 6, wherein the drawing unit surrounds a region containing the tissue or the cell classified as abnormal by the multiple view determination unit with a frame on the image data to actualize the region containing the tissue or the cell.

10. The diagnostic imaging assistance method according to claim 6, wherein the wide view image data and the narrow view image data in which a region containing the tissue or the cell classified as abnormal by the multiple view determination unit is actualized in the drawing unit are displayed on a display screen of an output unit side by side.

11. A diagnostic imaging assistance method comprising:
inputting narrow view image data obtained by capturing a cell of a diagnostic object to an input unit;
processing the narrow view image data input to the input unit by a feature extraction unit to extract a feature amount on an image of the cell;
classifying whether the cell is normal or abnormal by a single view determination unit from the feature amount of the narrow view image data extracted by the feature extraction unit;
capturing an image of a tissue containing a cell classified as abnormal by the single view determination unit to input wide view image data of the tissue to the input unit, the narrow view image data and the wide view image data comprising image data;
processing the wide view image data input to the input unit by a feature extraction unit to extract a feature amount on the image of the tissue;

classifying whether the tissue is normal or abnormal by the single view determination unit from the feature amount of the wide view image data extracted by the feature extraction unit;

classifying a lesion likelihood of the diagnostic object by a multiple view determination unit from a classification result of the narrow view image data and a classification result of the wide view image data classified by the single view determination unit;

actualizing a region containing the cell or the tissue classified as abnormal by the single view determination unit on the image data in a drawing unit; and storing the image data obtained by actualizing the region containing the cell or the tissue classified as abnormal in a recording unit.

12. The diagnostic imaging assistance method according to claim 11, wherein a learning unit creates a first identifier to classify whether the cell in the image data input to the input unit is a normal cell or an abnormal cell using the feature amount of the narrow view image data of a slice of the cell extracted by the feature extraction unit and a result obtained by classifying whether the cell is normal or abnormal by the single view determination unit, and a second identifier to classify whether the tissue in the image data input to the input unit is a normal tissue or an abnormal tissue using the feature amount of the wide view image data of a slice of the tissue extracted by the feature extraction unit and a result obtained by classifying whether the tissue is normal or abnormal by the single view determination unit.

13. The diagnostic imaging assistance method according to claim 11, wherein the single view determination unit calculates a deformed degree of the cell from the feature amount of the narrow view image data to classify whether the cell is normal or abnormal, and calculates a deformed degree of the tissue from the feature amount of the wide view image data to classify whether the tissue is normal or abnormal.

14. The diagnostic imaging assistance method according to claim 11, wherein the drawing unit surrounds a region containing the tissue or the cell classified as abnormal by the multiple view determination unit with a frame on the image data to actualize the region containing the tissue or the cell.

15. The diagnostic imaging assistance method according to claim 11, wherein the wide view image data and the narrow view image data in which a region containing the tissue or the cell classified as abnormal by the multiple view determination unit is actualized in the drawing unit are displayed on a display screen of an output unit side by side.

16. A remote diagnostic assistance system, comprising:
an image acquisition device including an image capturing unit to capture image data and a display unit; and
a server including the diagnostic imaging assistance apparatus according to claim 1,
wherein the image acquisition device transmits the image data to the server,
the server receives the transmitted image data, processes the image data by the diagnostic imaging assistance apparatus, stores images of a tissue and a cell determined and a determination result in a memory, and transmits the images and the determination result to the image acquisition device, and
the image acquisition device displays the determination result and the images of the tissue and the cell determined which are transmitted from the server on the display unit.

17. A network entrusting service provision system comprising:
an image acquisition/processing device including an image capturing unit to capture image data;
a server including the diagnostic imaging assistance apparatus according to claim 1; and
a display device,
wherein the image acquisition/processing device transmits the image data to the server,
the server receives the transmitted image data, processes the image data by the diagnostic imaging assistance apparatus, stores images of a tissue and a cell determined and an identifier in a memory, and transmits an identifier to the image acquisition/processing device, and
the diagnostic imaging assistance apparatus according to claim 1 in the image acquisition/processing device determines images of other tissues and cells using the received identifier transmitted from the server, and displays a determination result on the display device.

* * * * *